US012714788B2

(12) United States Patent
Anthony et al.

(10) Patent No.: US 12,714,788 B2
(45) Date of Patent: Aug. 25, 2026

(54) DRUG INJECTION APPARATUS, SYSTEMS AND METHODS

(71) Applicant: SOLUtion Medical, Inc., Ambler, PA (US)

(72) Inventors: Julia Anthony, Havertown, PA (US); Martin Bouliane, Ridgway, CO (US); Jonathan Kiel, Havertown, PA (US); Alexander Numann, Philadelphia, PA (US); Mikael Avery, Collingwood, NJ (US); Kirrily Haskard, Lewisham (AU); William Mason, Leichhardt (AU)

(73) Assignee: SOLUtion Medical, Inc., Ambler, PA (US)

( * ) Notice: Subject to any disclaimer, the term of this patent is extended or adjusted under 35 U.S.C. 154(b) by 1037 days.

(21) Appl. No.: 17/802,068

(22) PCT Filed: Feb. 26, 2021

(86) PCT No.: PCT/US2021/020123

§ 371 (c)(1),
(2) Date: Aug. 24, 2022

(87) PCT Pub. No.: WO2021/174143

PCT Pub. Date: Sep. 2, 2021

(65) Prior Publication Data

US 2023/0041970 A1 Feb. 9, 2023

Related U.S. Application Data

(60) Provisional application No. 62/981,811, filed on Feb. 26, 2020.

(51) Int. Cl.
*A61M 5/19* (2006.01)
*A61K 31/573* (2006.01)
(Continued)

(52) U.S. Cl.
CPC ............. *A61M 5/19* (2013.01); *A61K 31/573* (2013.01); *A61M 5/2033* (2013.01);
(Continued)

(58) Field of Classification Search
CPC .... A61M 5/19; A61M 5/2448; A61M 5/2033; A61M 2005/206; A61M 2005/3228;
(Continued)

(56) References Cited

U.S. PATENT DOCUMENTS 3,682,174 A * 8/1972 Cohen ............... B05C 17/00593 604/201
3,699,961 A * 10/1972 Szpur ................ A61M 5/31596 417/550

(Continued)

FOREIGN PATENT DOCUMENTS

EP 0 361 668 A1 4/1990
JP 54-016885 A 2/1979

(Continued)

OTHER PUBLICATIONS

Extended European Search Report dated Feb. 22, 2024 issued from the European Patent Office in corresponding International Application No. PCT/US2021/020123.

(Continued)

*Primary Examiner* — Nilay J Shah
(74) *Attorney, Agent, or Firm* — Troutman Pepper Locke LLP

(57) ABSTRACT

The disclosure relates to systems, methods and apparatus of storing, transporting, mixing, and injecting a drug as a solution, and in some embodiments, to a drug injection apparatus and system intended for use in mixing on demand a drug with a liquid, such as water, in a premeasured quantity and dosage, and injecting the drug mixture using an inte-
(Continued)

grated hypodermic needle assembly. Also provided are methods of using such apparatus and systems.

17 Claims, 9 Drawing Sheets

(51) Int. Cl.

| | |
|---|---|
| ***A61M 5/20*** | (2006.01) |
| ***A61M 5/24*** | (2006.01) |
| ***A61M 5/32*** | (2006.01) |
| *A61M 5/31* | (2006.01) |

(52) U.S. Cl.
CPC ........ *A61M 5/2459* (2013.01); *A61M 5/2466* (2013.01); *A61M 5/3271* (2013.01); *A61M 2005/2462* (2013.01); *A61M 2005/2474* (2013.01); *A61M 2005/3128* (2013.01)

(58) Field of Classification Search
CPC .............. A61M 5/3232; A61M 5/3234; A61M 5/3271; A61M 5/2466; A61M 2005/2474; A61M 2005/3128
See application file for complete search history.

(56) References Cited

U.S. PATENT DOCUMENTS

| | | | | |
|---|---|---|---|---|
| 4,643,721 | A | 2/1987 | Brunet | |
| 5,637,087 | A * | 6/1997 | O'Neil | A61M 5/284 604/82 |
| 2005/0075602 | A1 * | 4/2005 | Cherif-Cheikh | A61M 5/2448 604/87 |
| 2005/0177100 | A1 | 8/2005 | Harper et al. | |
| 2008/0171971 | A1 | 7/2008 | Diperna et al. | |
| 2015/0306362 | A1 * | 10/2015 | Battaglia | A61B 50/30 53/425 |
| 2018/0085531 | A1 | 3/2018 | Kramer et al. | |

FOREIGN PATENT DOCUMENTS

| | | | |
|---|---|---|---|
| JP | 2004-041568 | A | 2/2004 |
| WO | 2009103251 | A1 | 8/2009 |

OTHER PUBLICATIONS

International Search Report and Written Opinion dated May 25, 2021, from corresponding International Application No. PCT/US2021/020123.
Office Action issued in counterpart Japanese Patent Application No. 2022-551746 dated Jan. 29, 2025.

* cited by examiner

DRUG INJECTION APPARATUS, SYSTEMS AND METHODS

CROSS REFERENCE TO RELATED APPLICATION

This application claims priority to U.S. Provisional Application No. 62/981,811 filed on Feb. 26, 2020, which is incorporated by reference herein in its entirety.

FIELD OF THE INVENTION

The disclosure relates to a device comprising a needle for administration of an active agent into a subject, where the active agent in a solid or liquid form of an active agent in one compartment separated from a diluent or pharmaceutically acceptable carrier in another compartment, the device capable of exposing the active agent to the diluent or pharmaceutically acceptable carrier for mixing or dissolution prior to administration. The disclosure also relates to systems, methods and apparatus of storing, transporting, mixing, and injecting a drug as a solution, and in some embodiments, to a drug injection apparatus and system intended for use in mixing on demand a drug with a liquid, such as water, in a premeasured quantity and dosage, and injecting the drug mixture using an integrated hypodermic needle assembly. Also provided are methods of using such apparatus and systems.

BACKGROUND

Emergency injections have long been utilized in response to any number of forms of extremely time-sensitive, life-threatening events including overdose, anaphylaxis, angioedema or adrenal insufficiency (AI). The immediate need and essential nature of the active ingredients necessitate both accurate and rapid drug delivery. In fact, while naloxone auto-injectors (Evzio®) and epinephrine-containing auto-injectors (Epi-Pen® and Auvi-Q®) offer a more easily manipulated and administered dosing system, steroid injectors (Solu-Cortef® and Solu-Medrol®), due to their reliance upon reconstitution, while equally imperative, continue to suffer from cumbersome delivery systems that provide sub-optimal administration devices in terms of drug preparation and delivery.

To this point, steroid emergency injections, namely hydrocortisone, remains the drug of choice in adrenal insufficiency marked by conditions where the adrenal glands express an inability to produce adequate amounts of the glucocorticoid cortisol. Cortisol itself is released in response to both stress and hypoglycemia wherein this essential steroid is responsible for the production of glucose and for immunosuppression as well as, among other processes, glycogenesis, electrolyte balances, gastric acid secretion and can affect sleep, mood and stress levels. Conversely, a decrease in (or absence of) cortisol can result in weakness, fatigue, weight loss and depression while the complete absence of cortisol can precipitate adrenal shock or adrenal crisis, wherein the body lacks the ability to maintain homeostatic function, and an individual can exhibit severe lethargy, confusion, psychosis, cramping, diarrhea, vomiting, cramping, low blood sugar and other life threating sequelae up to and including death.

Up to now, patients living with Congenital Adrenal Hyperplasia (CAH), Addison's disease, and idiopathic adrenal insufficiency face challenges in the administration of their medication. Conventionally, to prepare hydrocortisone for intramuscular (IM) administration, the individual either injects bacteriostatic water or bacteriostatic sodium chloride into a sterile vial containing dry hydrocortisone powder or utilizes an Act-o-Vial® system, where the diluent in an upper vial is connectively attached to a lower vial containing active dry hydrocortisone ingredient. Both require arduous manipulation of disparate or conjoined vials, alike, for mixing, withdrawal and administration of the reconstituted mixture all within a life-critical, exceedingly short time period. Even in the case of the relatively simpler Act-o-Vial® drug mixing system, it requires an average of twelve user steps for injection, including (1) retrieve a needle and diluent/drug container, (2) depress the plastic cover above the diluent containing vial downward (releasing the diluent into the dry ingredient containing vial below), (3) mix the dry powder and solution, (4) remove the plastic cover, (5) sterilize the needle receiving stopper, (6) insert the needle through the stopper center, (7) withdraw the dose and, finally, (8) inject the appropriate dose intramuscularly. Because of the complexity of the system, the Act-o-Vial® delivery system requires a trained medical personnel to ensure proper retrieval and administration of a potentially life-saving drug. The Act-o-Vial® delivery system is not designed to be utilized by a layperson or an individual living with adrenal insufficiency.

SUMMARY OF THE EMBODIMENTS

The disclosure relates to systems, methods and apparatus involving transportation, storage, mixture, and injection of a drug to a patient, such as involving administration to the patient of a single dose of the drug transported, stored, mixed and injected using a drug injection device.

Steroid emergency injections, namely hydrocortisone, remains the drug of choice in adrenal insufficiency marked by conditions where the adrenal glands express an inability to produce adequate amounts of the glucocorticoid cortisol. A decrease in, or absence of, cortisol can result in numerous conditions, including weakness, fatigue, weight loss and depression, while the complete absence of cortisol can precipitate adrenal shock or adrenal crisis, which may be life threating. It is against this backdrop that the importance of immediate administration of exogenous cortisol (i.e., hydrocortisone) becomes imperative and mandatory. To date, hydrocortisone is available to inpatient recipients via intravenous injection, by intravenous infusion, or by intramuscular (IM) injection, but available only practically to outpatient recipients for acute short-term conditions through a prepared reconstitutable intramuscular injection from doses typically between 100 mg to 500 mg.

Intending to address the shortcomings of the prior art devices, the disclosure focuses on creating more patient-friendly and effective drug delivery systems. The disclosure aims to improve the administration efficacy of lifesaving injectable medication with twist-to-mix delivery systems and devices to benefit millions people worldwide living with Congenital Adrenal Hyperplasia (CAH), Addison's disease, and idiopathic adrenal insufficiency. Exemplary embodiments of the disclosed systems and devices require as few as four steps for injection and can be designed for people experiencing an adrenal crisis and their caregivers.

The present disclosure is directed to remedy primarily the inadequacies in the area of emergency injectable steroids. The disclosure is also directed to further advance the efficient and effective administration of other emergency medications (e.g., epinephrine and naloxone) and non-emergency medications including, but not limited to non-emergency steroids, antibiotics, analgesics, disease specific treatments (e.g., MS treatments, psoriasis treatments), insulins, glycoproteins, immunomodulators, G-CSFs, erythropoietin (Epogen®, Procrit®), biologics, antihypertensives, vaccines, hormones (including birth control), anti-hormones, sedatives, antiepileptics, anti-neoplastics, insecticidal agents (e.g., dobutrex), anti-psychotics, detoxing agents, cosmetics, selective serotonin reuptake inhibitors (SSRIs), proton-pump inhibitors (PPIs), anesthetics, diuretics, anti-diuretics, blood thinners (e.g., low molecular heparin), streptokinase, and the like, alone or in combination, whether in a liquid form, reconstitutable form or otherwise. In some embodiments, the systems and devices of the disclosure are used to deliver medications historically using the Act-o-Vial® system, namely Methylprednisolone for Multiple Sclerosis, certain cancers, and autoimmune conditions. In some embodiments, the systems and devices of the disclosure are used to deliver Glucagon used in hypoglycemic emergencies. In some embodiments, the systems and devices of the disclosure are used to deliver Ticarcillin used to treat high morbidity infections. In some embodiments, the systems and devices of the disclosure are used to deliver Chlordiazepoxide used to treat alcohol withdrawal symptoms. In some embodiments, the systems and devices of the disclosure are used to deliver Desoxycorticosterone pivalate used in veterinary emergencies. In some embodiments, the systems and devices of the disclosure are used for in-vitro fertilization treatments.

As described below, embodiments of the present disclosure include the use of a medication transportation and storage container, a drug mixing system, and a drug injection assembly, using apparatus, assemblies, systems and methods different from those of the prior art.

While the disclosure sets forth the best mode or modes contemplated of carrying out the various embodiments disclosed herein to enable a person skilled in the art to practice the present disclosure, the preferred embodiments are, however, not intended to be limiting, but, on the contrary, are included in a non-limiting sense apt to alterations and modifications within the scope and spirit of the disclosure and appended claims.

In accordance with an aspect of the disclosure, an apparatus is disclosed for transportation, storage, mixture, and injection of a drug to a patient, wherein the apparatus comprises: a transportation assembly, a storage assembly, a mixture assembly, and an injection assembly. The transportation assembly is adapted to provide a convenient mode of transporting the drug prior to administration of the drug to the patient. The storage assembly is adapted to properly store the drug and mixing ingredients within the transportation assembly prior to mixing the drug and mixing ingredients to create a drug-in-solution just before injecting the mixture into the patient. The mixture assembly is adapted to properly mix the drug and mixing ingredients to create the drug-in-solution within the transportation assembly in preparation of injecting the mixture into the patient. The injection assembly is adapted to properly inject the drug-in-solution into the patient once the mixture is created.

In accordance with an aspect of the disclosure, a method is disclosed for using the apparatus disclosed herein for transportation, storage, mixture, and injection of a drug to a patient, wherein the apparatus comprises: a transportation assembly, a storage assembly, a mixture assembly, and an injection assembly, and wherein the method comprises providing the apparatus, engaging the mixture assembly to mix the drug and create a drug-in-solution in preparation to administer the drug to the patient, and engaging the injection assembly to inject the drug-in-solution into the patient. In some embodiments, the method further comprises disengaging a safety device prior to engaging the injection assembly to inject the drug-in-solution into the patient.

In accordance with an aspect of the disclosure, a method is disclosed for assembling an apparatus for transportation, storage, mixture, and injection of a drug to a patient, wherein the apparatus comprises: a transportation assembly, a storage assembly, a mixture assembly, and an injection assembly, and wherein the method comprises: providing and assembling the transportation assembly; providing and assembling the storage assembly, providing and assembling the mixture assembly, and providing and assembling the injection assembly.

In accordance with an aspect of the disclosure, a system is disclosed for assembling an apparatus for transportation, storage, mixture, and injection of a drug to a patient, wherein the apparatus comprises: a transportation assembly, a storage assembly, a mixture assembly, and an injection assembly, and wherein the system comprises: means for assembling the transportation assembly; means for assembling the storage assembly, means for assembling the mixture assembly, and means for assembling the injection assembly.

The disclosure accordingly provides a device comprising: (a) a first compartment and a second compartment, each of the first and second compartments defining a first and second cavity, respectively, separated by and in fluid communication with a first opening; (b) a needle assembly; and (c) an insertion rod positioned in the first compartment operably connected to a movable element, wherein the first opening is covered by a seal. In some embodiments, the insertion rod of the disclosed device comprises two oppositely directed faces, the first face physically in contact with the movable element and the second face positioned within the first cavity; wherein the second face comprises a protrusion and at least one valve distally positioned from the protrusion. In some embodiments, the protrusion in the second face of the insertion rod has a beveled surface. In some embodiments, the movable element of the disclosed device is physically positioned adjacent to the insertion rod, and the insertion rod is movable upon depression of the movable element toward a direction along a longitudinal axis parallel to and within the first compartment and second compartments.

In some embodiments, the second compartment of the disclosed device comprises an active agent and the first compartment of the disclosed device comprises a pharmaceutically acceptable carrier. In some embodiments, the second compartment comprises a pharmaceutically acceptable carrier and the first compartment comprises an active agent. In some embodiments, both the first compartment and the second compartment each comprises one or a plurality of active agents. In some embodiments, both the first compartment and the second compartment each comprises: one or a plurality of active agents and one or a plurality of pharmaceutically acceptable carriers. In some embodiments, the second compartment comprises an active agent in solid or semisolid form and the first compartment comprises a pharmaceutically acceptable carrier in liquid form. In some embodiments, the second compartment comprises an active agent in liquid form and the first compartment comprises a pharmaceutically acceptable carrier in liquid form. In some embodiments, the active agent comprised in the disclosed device is lyophilized.

In some embodiments, the disclosed device further comprises a third compartment defining a third cavity adjacent to and separated from the second compartment by a second opening covered by a second seal. In some embodiments, the second seal is a movable plug in operable connection to the movable element and, whereupon depression of the movable element, allows for displacement of the movable plug and fluid communication between the second and third compartments. In some embodiments, depression of the movable element allows for displacement of the movable plug, insertion rod and fluid communication between the second and third compartments.

In some embodiments, the third compartment of the disclosed device comprises the needle assembly; the needle assembly comprising a spring and a needle in operable connection to the spring; wherein the needle comprises a first fluid opening within the third cavity and an oppositely facing second fluid opening positioned away from the first and second cavities. In some embodiments, the first and second fluid openings are covered by a movable seal in operable connection to the movable element, such that depression of the movable element to the first and second predetermined positions causes displacement of the first and second seals respectively.

In some embodiments, the disclosed device is in a first operable condition and comprises a first, second and third compartment, the first and second compartments in fluid communication with each other by a first opening comprising a first seal; the second and third compartments in fluid communication with each other by a second opening covered by a second seal; wherein the second compartment is positioned between the first and third compartments on opposite facing sides of the second compartment; wherein the movable element is a fully extended position relative to the lateral orientation of the device, wherein the first compartment comprises a pharmaceutically acceptable carrier, the second compartment comprises one or a plurality of active agents, the third compartment comprises needle assembly, and wherein the first and second seals covering each of the first and second openings are fully intact preventing fluid flow from one compartment to another compartment. In some embodiments, the disclosed device is in a second operable condition and comprises a first, second and third compartment, the first and second compartments in fluid communication with each other by a first opening; the second and third compartments in fluid communication with each other by a second opening covered by a second seal; wherein the second compartment is positioned between the first and third compartments on opposite facing sides of the second compartment; wherein the movable element is in a partially depressed position relative to the lateral orientation of the device, wherein the first and second compartments comprises a pharmaceutically acceptable carrier and one or a plurality of active agents; wherein the third compartment comprises needle assembly, and wherein the second seal covers the second opening preventing fluid flow from the third compartment into the first or second compartments. In some embodiments, the disclosed device is in a third operable condition and comprises a first, second and third compartment, the first, second and third compartments are in fluid communication with each other; wherein the second compartment is positioned between the first and third compartments on opposite facing sides of the second compartment; wherein the movable element is in a partially depressed position relative to the lateral orientation of the device such that the insertion rod has punctured the second seal, wherein the first, second and third compartments comprise a pharmaceutically acceptable carrier and one or a plurality of active agents; wherein the third compartment comprises the needle assembly, and wherein the second seal has been punctured or disposed from its position over the second opening and the needle assembly is exposed to the active agent and pharmaceutically acceptable carrier. In some embodiments, the disclosed device is in a fourth operable condition and comprises a first, second and third compartment, the first, second and third compartments are in fluid communication with each other; wherein the second compartment is positioned between the first and third compartments on opposite facing sides of the second compartment; wherein the movable element is in a fully depressed position relative to the lateral orientation of the device and the needle of the needle assembly is exposed. In some embodiments where the disclosed device is in the second, third, or fourth position, the active agent comprised in the disclosed device is dissolved in one or a plurality of pharmaceutically acceptable carriers.

In some embodiments, the active agent comprised in any of the disclosed device is chosen from any one or combination of active agents from Table 1. In some embodiments, the active agent is chosen from any one or combination of active agents from Table 1 in a dosage identified in Table 1. In some embodiments, the active agent is a cortisone or cortisone derivative thereof. In some embodiments, the cortisone derivative is hydrocortisone sodium succinate wherein the derivative is in a dosage of from about 50 mg to about 250 mg in weight or from about 25 mg/mL to about 150 mg/mL in a weight to volume solution of active agent in pharmaceutically acceptable carrier.

In some embodiments, the first or the second compartment of the disclosed device comprises a pharmaceutically acceptable carrier in fluid form with a viscosity of from about 1 cP to about 150 cP.

In some embodiments, the disclosure provides a method of treating and/or preventing a disease or disorder in a subject in need thereof comprising administering one or a plurality of active agents into the subject by any of the devices disclosed herein. In some embodiments, the disclosure provides a method of treating a subject in need of administration of one or a plurality of active agents comprising administering a pharmaceutically effective amount of the one or plurality of active agents by any of the devices disclosed herein. In some embodiments, the disclosure provides a method of treating cortisol depletion in a subject in need thereof comprising administering to the subject a cortisone or cortisone derivative thereof through any of the devices disclosed herein. In some embodiments, the cortisol depletion in the subject is caused by Addison's disease, Congenital adrenal hyperplasia, Autoimmune adrenalitis, Adrenalectomy, Adrenomyeloneuropathy, Adrenoleukodystrophy, Adrenal Tumors, Schmidt Syndrome, Hyperaldosteronism, Pituitary Tumors, Pituitary Cysts, and/or Critical-illness Related Corticosteroid Insufficiency. In some embodiments, the disclosure provides a method of treating a cortisol disorder in a subject in need thereof comprising administering to the subject a cortisol or cortisol derivative by use of any of the devices disclosed herein. In some embodiments, the step of administering in any of the disclosed methods of treatment comprises: depressing the movable element of the disclosed device to a first predetermined position, a second predetermined position and a third predetermined position; wherein the device comprises: a first compartment, a second compartment and a third compartment, each of the first, second and third compartments defining a first, second and third cavity, respectively; the first and second compartments separated by and in fluid communication with a first opening, and the second and third compartments separated by and in fluid communication with a second opening; wherein each of the first opening is covered by a first seal and the second opening is covered by a second seal; wherein the third compartment comprises a needle assembly comprising a spring and a needle in operable connection to the spring; wherein depressing the movable element to the first predetermined position causes the insertion rod to displace the first seal from the first opening and expose the first opening between the first and second compartment resulting in fluid communication between the first and second compartments; and wherein depressing the movable element to the second predetermined position causes the insertion rod to displace the second seal from the second opening and expose the second opening between the second and third compartment resulting in fluid communication between the second and third compartments; and wherein depressing the movable element to a third predetermined position causes ejection of the contents of the third compartment through the needle assembly. In some embodiments, the disclosed method further comprises a step of unlocking the needle assembly prior to depressing the movable element to the third predetermined position.

In some embodiments, the disclosure provides a method of treating congenital adrenal hyperplasia or Addison's disease in a subject in need thereof comprising administering to the subject a cortisone or cortisone derivative thereof through any of the devices disclosed herein.

The disclosure further provides a method of manufacturing any of the devices disclosed herein comprising positioning the active agent or agents in a sterile or aseptic environment. In some embodiments, the method further comprises weighing the active agent or agents. In some embodiments, the method further comprises affixing the first and second compartments. In some embodiments, the method comprises attaching the first and second compartments in a sterilized environment by compression or screw into a fastener.

The disclosure also provides a method of administering an active agent to a subject in need thereof through any of the devices disclosed herein comprising: (a) depressing the movable element to a first predetermined position; and (b) depressing the movable element to a second predetermined position; wherein the first predetermined position creates displacement sufficient for the insertion rod to puncture the first seal, such that the first and second compartments are in fluid communication; and wherein the second predetermined position creates a displacement sufficient to displace the movable seal, thereby allowing fluid communication between the second and third compartments. In some embodiments, the second predetermined position creates a displacement sufficient to load the spring in the third compartment with a force from about 0 to about 100 Newtons.

The disclosure additionally provides a device comprising: (a) a first compartment, a second compartment, and a third compartment, each of the first, second and third compartments defines a first, second and third cavity, respectively, and the second compartment is adjacently positioned between the first and third compartments; (b) a needle guard assembly operably functional within and at least partially housed in the third cavity and comprising a needle operably attached to a spring; and (c) an insertion rod positioned in the first compartment operably connected to a movable element, the insertion rod and movable element movable along a longitudinal axis of the first, second and third compartments; wherein the first and second compartments are in fluid communication through a first opening; wherein the second and third compartments are in fluid communication through a second opening; the first opening covered by a first seal and the second opening covered by a second seal. In some to embodiments, the first compartment comprises one or a plurality of active agents; and the second compartment comprises one or a plurality of pharmaceutically acceptable carriers. In some embodiments, the first compartment comprises one or a plurality of pharmaceutically acceptable carriers; and the second compartment comprises one or a plurality of active agents. In some embodiments, the first, second and third compartments are cylindrically aligned along the longitudinal axis of the cavities. In some embodiments, the needle guard assembly of the device comprises a spring, a needle sheath, and an interior surface comprising one or a plurality of track elements in operable connection to the needle, such track elements capable of guiding movement of the needle through the needle sheath after movement of the spring.

BRIEF DESCRIPTION OF THE DRAWINGS

By reference to the appended drawings, which illustrate exemplary embodiments of the disclosure, the detailed description provided below explains in detail various features, advantages and aspects of this disclosure. As such, features of this disclosure can be more clearly understood from the following detailed description considered in conjunction with the following drawings, in which the same reference numerals denote the same, similar or comparable elements throughout. The exemplary embodiments illustrated in the drawings are not necessarily to scale or to shape and are not to be considered limiting of its scope, for the disclosure may admit to other equally effective embodiments having differing combinations of features, as set forth in the accompanying claims.

Figure 1A:
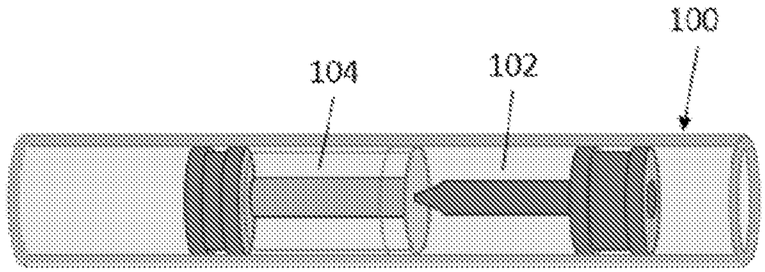
FIG. 1A shows a side cross sectional view of one embodiment of the device disclosed herein. 100: Three chambered system allowing for the containment and mixing of one or more solid or liquid materials. 102: First chamber that contains a liquid or solid material, which is separated from a second chamber 104 by a barrier. 104: Second chamber that contains a liquid, or solid material. This chamber is separated from chamber 102 by a barrier.

Insertion rod 204 is likely comprised of or surrounded by sealant material to prevent fluid flow going behind the insertion rod. 206: Seal between chambers 216 and 208 that prevents material transfer between the two chambers until the barrier is penetrated by insertion rod 204. 208: Second chamber that houses liquid, solid, semisolid or gaseous material to be combined with the material held in chamber 216 after penetration of seal 206. 210: Third device chamber where materials from chamber 208 and 216 are combined after activation of the device. 212: Spring that compresses upon material transfer into chamber 210 after penetration of seal 206 and material combination occurs. 214: Moveable seal assembly that moves through chamber 210 upon combination of the materials in chambers 208 and 216. Seal assembly 214 compresses spring 212 upon moving inward into chamber 210. 216: First chamber in device. Chamber could contain liquid or solid material that is to be combined with material in chamber 208 after insertion rod 204 penetrates seal 206. 218: Housing that contains the three chambered system of 216, 208, and 210, and activation system 202.

Figure 2A:
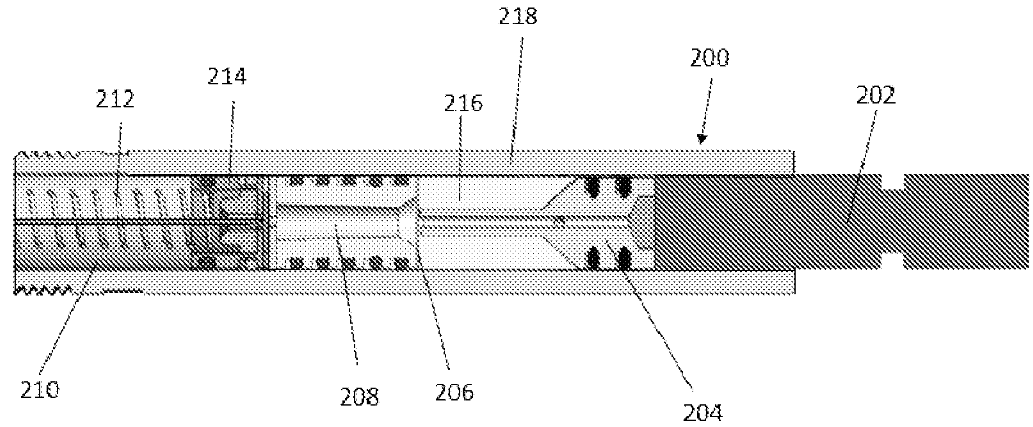
FIG. 2A shows a side cross sectional view of another embodiment of the device disclosed herein, which further comprises moveable components, chamber barriers, seals, and other components associated with an auto-injector. 200: Three chambered system including a housing, plunger, mechanisms separating the three chambers, a compression system to activate combination of materials held in the first two chambers and move the materials into the third chamber. 202: An activation system to begin the combination of materials held in chambers 216 and 208 and move the materials into chamber 210. 204: An insertion rod that penetrates seal 206 and allows material transfer between chambers 216 and 208. The insertion rod will push into chamber 208 to aid in pushing the liquid from 216 into 208.
Figure 2B:
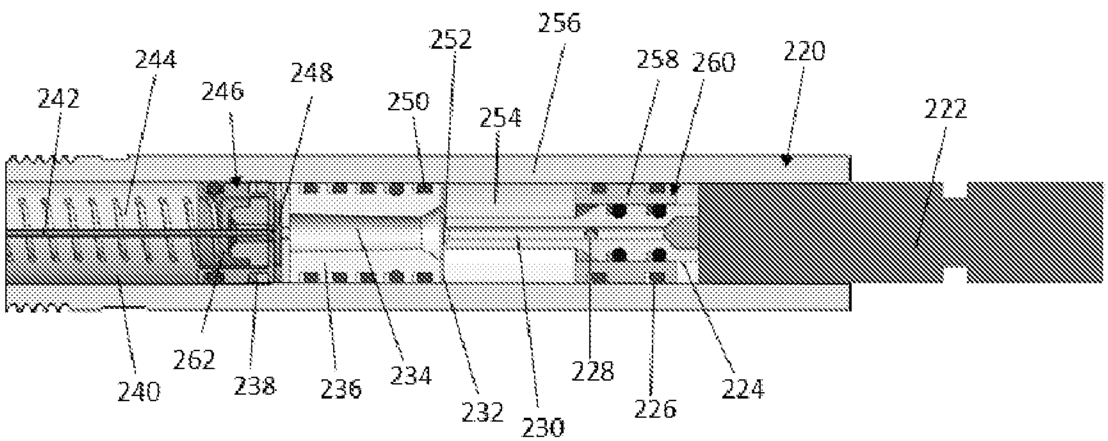

FIG. 2B shows a side cross sectional view of another embodiment of the device disclosed herein where the insertion rod that breaks the seal 226 is two components instead of one. 220: Another embodiment of the three chambered system for mixing two materials. 222: An activation system to begin the combination of materials held in chambers 254 and 234 and move the materials into chamber 210. 224: Insertion rod assembly that penetrates seal 232 to allow materials in chamber 254 and 234 to be combined. 226: Seal component to prevent fluid from moving backwards through device. 228: Fluid vent to allow fluid transfer between chambers 254 and 234. 230: Fluid path through insertion rod 224 to allow fluid transfer between chambers 254 and 234. 232: Seal between chambers 254 and 234 that prevents material transfer between the two chambers until the barrier is penetrated by insertion rod 224. 234: Second chamber that houses liquid or solid material to be combined with the material held in chamber 254 after penetration of seal 232. 236: Housing for chamber 234. Housing may be encased on the sides or the ends by material transfer barriers. 238: Slidable seal for moveable assembly 246. This seal prevents fluid from passing around its edges. 240: Third device chamber where materials from chamber 254 and 234 are combined after device activation. 242: Needle for injection of combined materials. 244: Spring that compresses upon filling of chamber 240 and subsequent movement of assembly 246 through chamber 240. 246: Seal assembly that acts as a barrier for chamber 234 prior to device activation. After activation, the seal is a wall for chamber 240, and then it is the compression mechanism to drive the combined materials out of the device. 248: Seal that prevents material entry into needle 242 until the seal is penetrated by the movement of assembly 246 upon device activation. 250: seal material on chamber housing 236. 252: Entry point of insertion rod into chamber 234. 254: First chamber containing material to be combined with material in chamber 234. 256: Housing containing mixing chambers, materials, and all device assemblies. 258: external housing for insertion rod 224 which allows the rod to move internally and may contain seals. 260: Insertion rod assembly. 262: Needle guide and spring attachment.

Figure 3A:
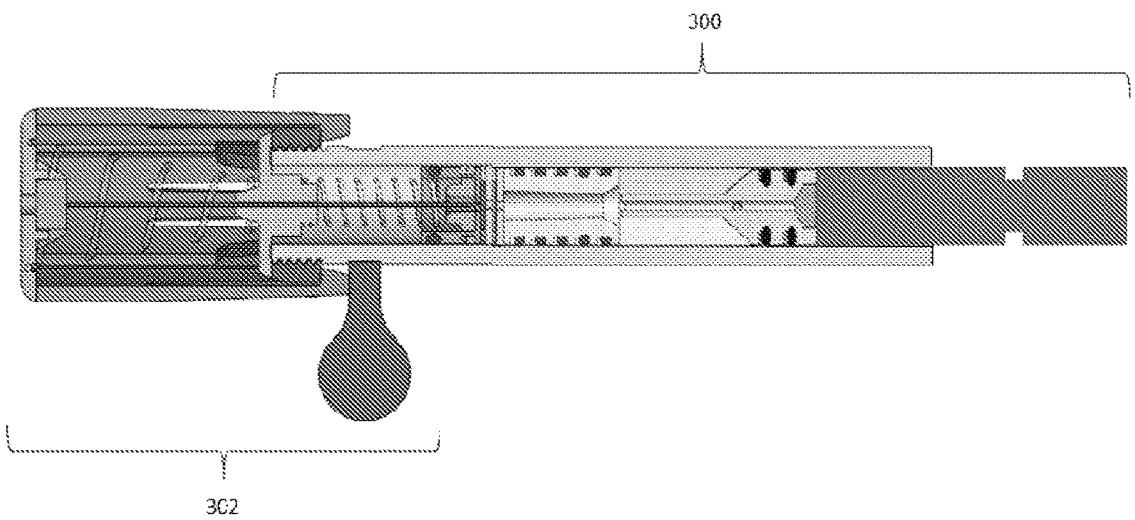
Figure 3B:
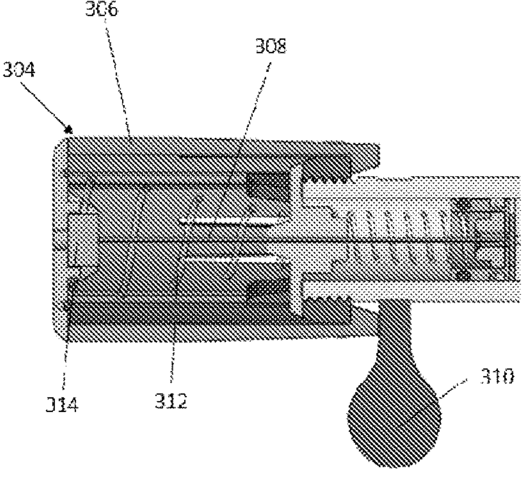
Figure 3C:
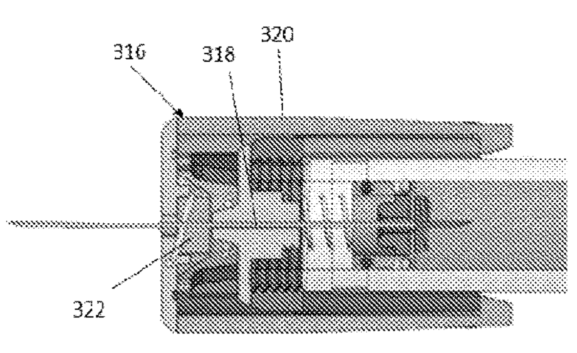
Figure 3D:
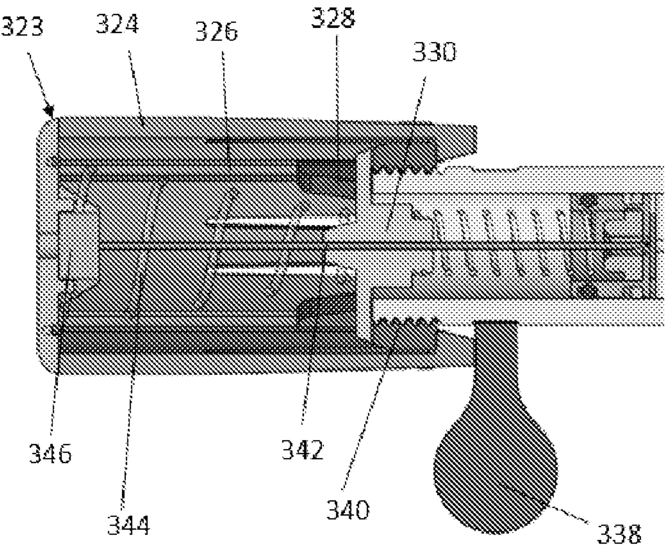
Figure 3E:
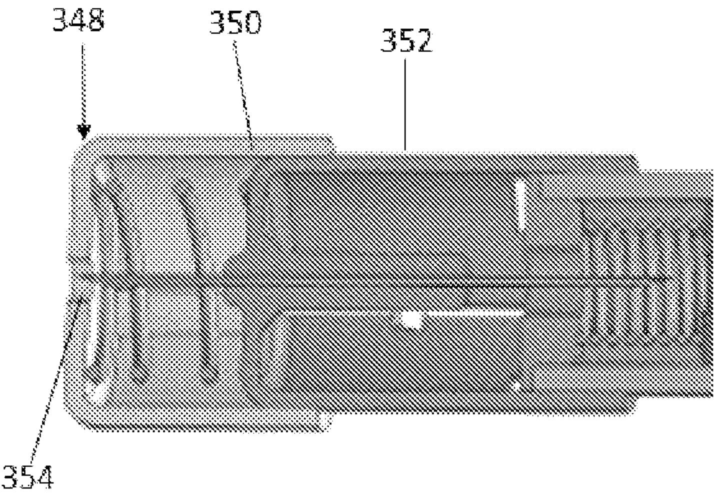

FIG. 3A shows a side cross sectional view of another embodiment of the device disclosed herein with a needle assembly having a needle guard 302 attached to the main device 300. 300: Device assembly for mixing two materials. 302: Needle assembly and needle guard for injection of two combined material. A more detailed view of the needle assembly and needle guard of this embodiment is shown in FIG. 3B. 304: Needle guard assembly that prevents fluid leaving the device and inhibits accidental injections. In this condition the guard is extended over the needle. 306: Needle guard housing that conceals needle 308 and retracts to allow for injection. 308: Injection needle. 310: Safety clip that prevents the needle guard from being activated prior to removal. 312: Compression spring that holds needle guard 304 in place and pushes needle guard 304 back over needle once injection is complete. 314: seal that prevents fluid entry into needle 308. FIG. 3C shows a condition in which the device of FIG. 3A is activated and the components are combined, but injection is yet begun. 316: Needle guard assembly that prevents fluid leaving the device and inhibits accidental injections. In this condition the guard housing is retracted to allow for injection. 318: Injection needle. 320: Needle guard housing that conceals needle 318 and retracts to allow for injection. 322: seal that prevents fluid entry into needle 318. A more detailed view of the needle assembly and needle guard is shown in FIG. 3D. 323: Needle guard assembly that prevents fluid leaving the device and inhibits accidental injections. In this condition the guard is extended over the needle. 324: Needle guard housing that conceals needle 342 and retracts to allow for injection. 326: Guide tracks to allow for needle guard to slide into place using guard guides 328. 328: Needle guard guides for guide tracks 326. 330: Needle stabilizer and attachment. 338: Safety clip that prevents needle guard housing 324 from retracting prior to intended use. 340: connection between needle guard assembly and injection device. 342: Injection needle. 344: Compression spring to push needle guard into place around needle. 346: Seal that prevents liquid entering or leaving the needle prior to injection. FIG. 3E shows another embodiment of the needle assembly and needle guard. 348: Another embodiment of the needle guard assembly that prevents fluid leaving the device and inhibits accidental injections. In this condition the guard is extended over the needle. 350: Needle guard housing that conceals a needle and retracts to allow for injection. 352: device housing, which also acts as a needle guard guide. 354: Needle exit that can contain a seal to prevent fluid entering or leaving the injection needle.

Figure 4:
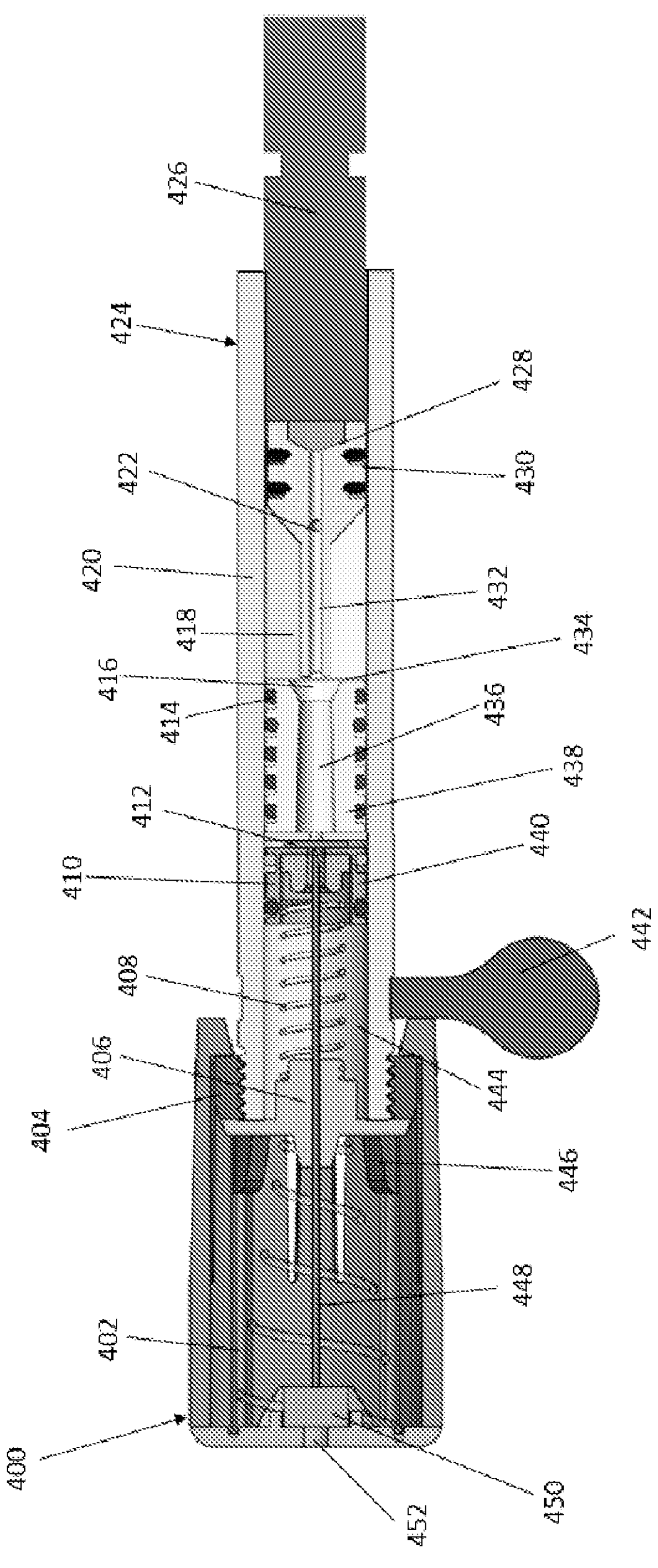

FIG. 4 shows a side cross sectional view of an embodiment with the device body, needle assembly and guard attached. 400: Needle guard assembly that prevents fluid leaving the device and inhibits accidental injections. In this condition the guard is extended over the needle. 402: Guide tracks to allow for needle guard to slide into place using guard guides 446. 404: Needle guard attachment point to main device. 406: Needle stabilizer and attachment. 408: Spring that compresses upon filling of chamber 444 and subsequent movement of assembly 410 through chamber 444. 410: Moveable seal assembly. 412: Seal that prevents material entry into needle 448. 414: Seal material on chamber 438. 416: Beveled entry point for insertion rod 428. 418: First device chamber. 420: Main device housing. 422: Fluid vent to allow fluid transfer between chambers 418 and 436. 424: Embodiment of the three chambered system for mixing two materials with needle assembly and guard. In this embodiment the materials have not been mixed. 426: An activation system to begin the combination of materials. 428: Insertion rod, 430: Seal around insertion rod. 434: Breakable seal between chambers 418 and 436. 436: Second device chamber. 438: Second chamber housing. 440: Slidable seal for moveable assembly 246. 442: Safety clip that prevents the needle guard from being activated prior to removal. 444: Third device chamber. 448: Needle for injection. 450: Seal that prevents fluid entry into needle 448. 452: Exit point for needle from needle guard.

Figure 5A:
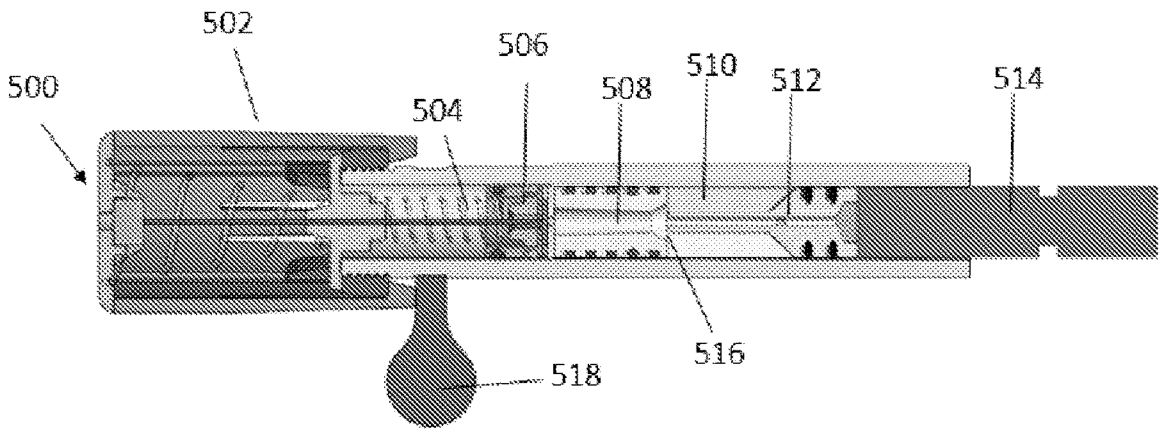

FIG. 5A shows a side cross sectional view of a first operable condition of the device disclosed herein. 500: First operable condition before the device has been activated. 502: Needle guard housing extended around the needle. 504: Combination chamber that is empty in this condition. 506: Moveable seal assembly that is acting as a barrier between chamber 508 and 504. 508: Chamber 508 containing the material to be combined with material in chamber 510. 510: Chamber containing material to be combined with material in chamber 508. 512: Insertion rod to break seal 516 and push material from chamber 510 into 508. 514: Activation assembly, which may be a plunger, screw system or some other type of method to compress the device and move the materials to be combined into chamber 504. 516: Seal between chambers 510 and 508. 518: Safety clip that prevents needle guard 502 from retracting.

Figure 5B:
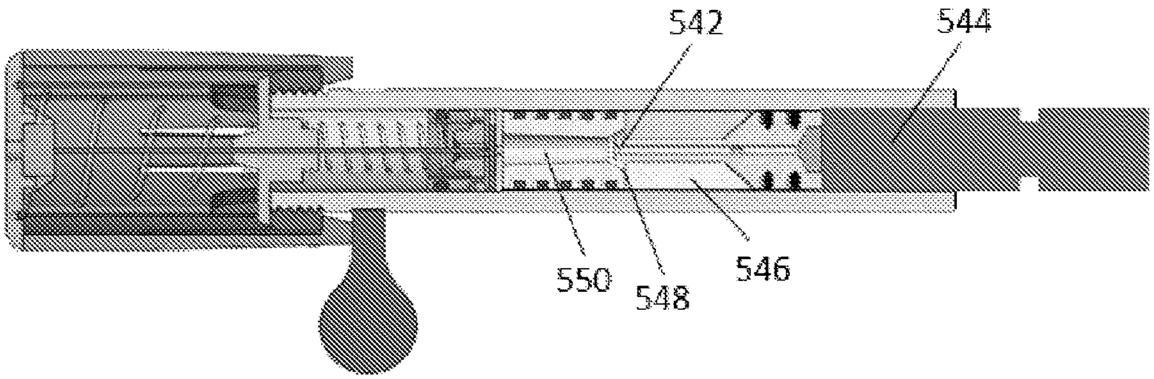

FIG. 5B shows a side cross sectional view of a second operable condition of the device disclosed herein. 542: Partially inserted insertion rod into chamber 546. 544: Activation assembly, which may be a plunger, screw system or some other type of method to compress the device and move the materials to be combined. 546: First device chamber. 548: Broken seal allowing chambers 550 and 546 to be in fluid contact. 550: Second device chamber.

Figure 5C:
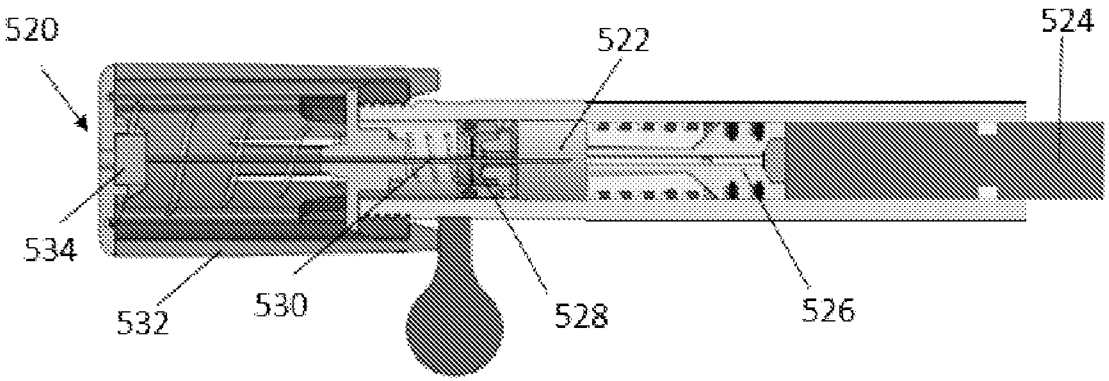

FIG. 5C shows a side cross sectional view of a third operable condition of the device disclosed herein. 520: Third operable condition in which the device has been activated, the materials are combined but not injected. 522: Combination chamber containing material from first two chambers. 524: Compression assembly that has been activated to allow for materials in first two chambers to be combined. 526: Insertion rod has completely moved through the first chamber to push all material through the second chamber and into chamber 522. 528: Seal assembly that has moved from the input of material from the first two chambers to create space in chamber 522 for the combined materials. 530: Compression spring that is now loaded to inject the combined materials once the needle guard 532 is retracted. 532: Needle guard in the unretracted position preventing the combined materials in chamber 522 from being removed from chamber 522 through the needle. 534: Seal that prevents material in chamber 522 from being removed through the needle.

Figure 5D:
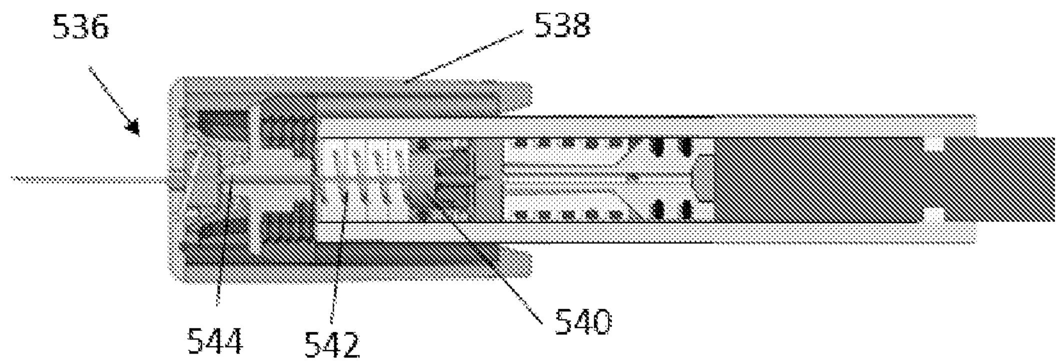

FIG. 5D shows a side cross sectional view of a fourth operable condition of the device disclosed herein. 536: Forth operable condition where the needle guard has been retracted and the combined materials have been forced out of the combination chamber. 538: Needle guard that has been retracted to expose the needle and allow for combined liquids to be forced out of the device. 540: Seal assembly has moved back into the device to force the combined liquids out of the device through the needle. 542: Compression spring has moved back into the device to force the combined materials out of the device. 544: Injection needle.

Figure 6:
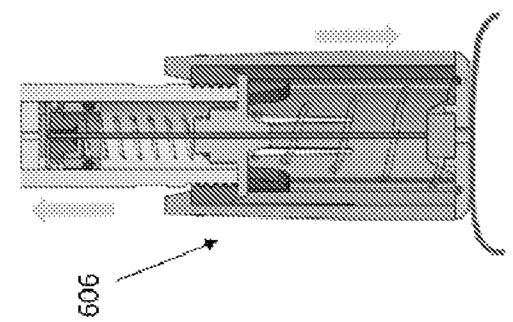
Figure 6:
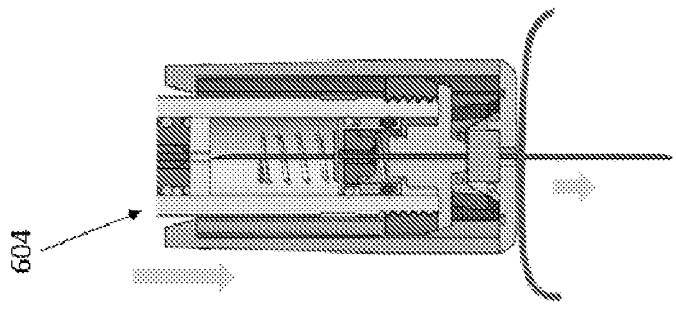
Figure 6:
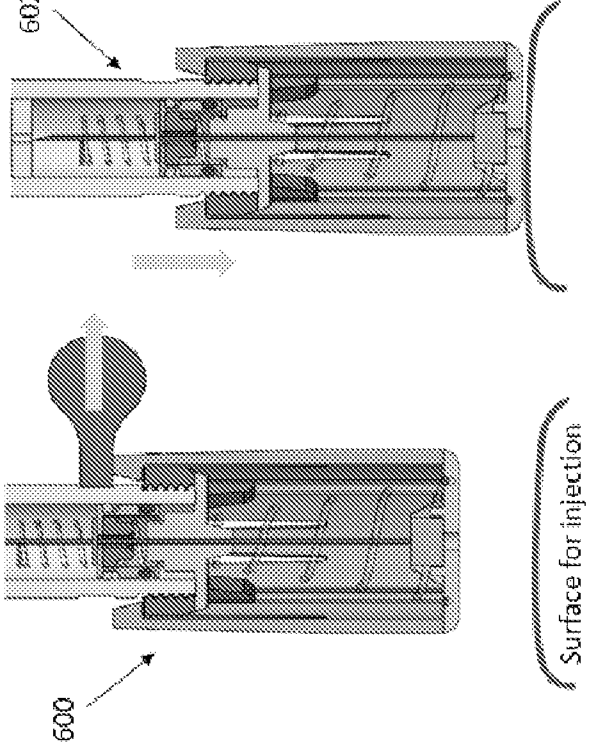

FIG. 6 shows side cross sectional views of the three main operable conditions of the device disclosed herein plus the final state where the device is removed from the injection site. 600: Operable condition prior to removal of the safety pin. The device has been activated and materials for injection are combined as indicated by the presence of the movable seal assembly near at the bottom of the third chamber. 602: The safety pin has been removed and the device can now be depressed against a surface, such as a patient's skin, for injection. 604: The device has been pushed onto a patient or other surface causing the needle guard to retract and the needle to enter the injection volume. The device is held into position until the injection is complete. 606: After all liquid has been injected, the device is moved upwards causing the needle guard to extend and cover the needle again. Injection is complete as noted by the presence of the moveable seal assembly farther from the bottom of the device.

Figure 7:
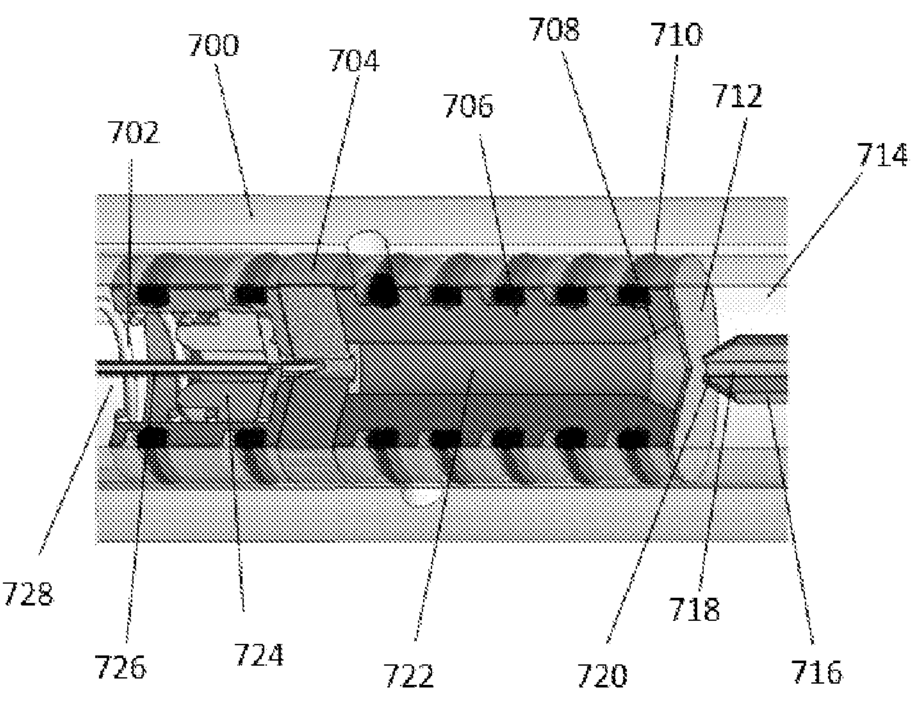

FIG. 7 shows a side cross sectional view of the internal components of the second chamber 722 of one embodiment of the device disclosed herein and how it resides between the other two chambers 714 and 728. 700: Internal assembly of the second chamber and associated components. 702: Compression spring that holds seal assembly 724 in position and allows for forcing combined materials out of device from chamber 728 during injection. 704: Seal that prevents transfer of material from chamber 722 into 728 and prevents fluid entry into needle 726. 706: housing for chamber 722. 708: Entry point for insertion rod 714 into chamber 722. 710: Seal surrounding chamber 710 preventing fluid flow. 712: Seal preventing material transfer between chamber 714 and 722. 714: First chamber in device containing material to be combined with that in chamber 722. 716: Insertion rod to penetrate seal 712 and force material from 714 into 722. 718: Fluid path to allow fluid transfer between chamber 720 and 714. 720: Piercing point to allow for penetration of seal 712. 722: Chamber containing material to be combined with material in 714. 724: Seal assembly that acts as a barrier between 728 and 722, as well as pushes fluid out of the device when injection is occurring. 726: Injection needle. 728: Combination chamber where the combined materials from 714 and 722 wait to be injected.

Figure 8:
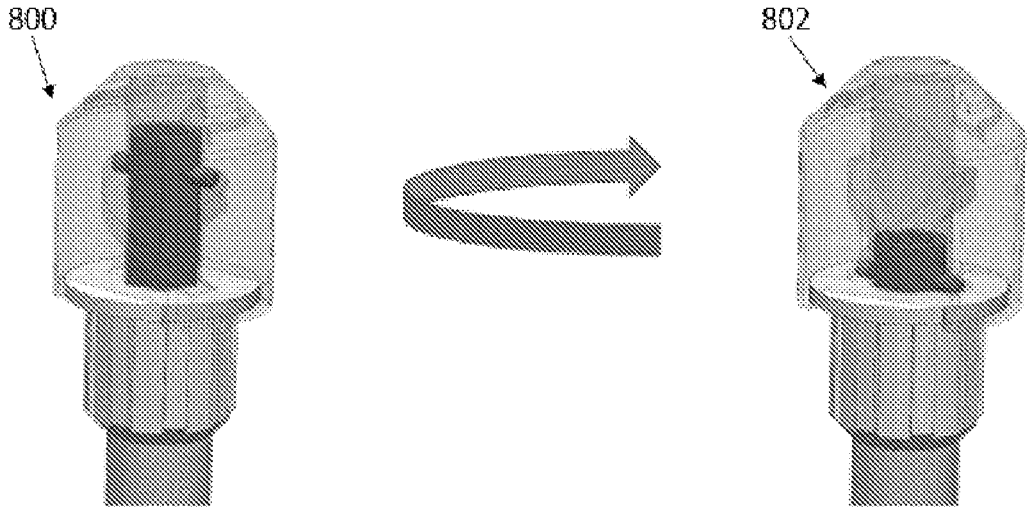

FIG. 8 shows a side cross sectional view of one embodiment of the device disclosed herein which uses a screw mechanism to drive a plunger downward. 800: Another embodiment of the activation assembly where the device is twisted and a screw mechanism forces a plunger downward. This is the device prior to activation. 802: The activation assembly after activation and the plunger is pushed downward forcing the combination of the two materials.

DETAILED DESCRIPTION OF THE EMBODIMENTS

The disclosure relates to systems, methods and apparatus for storing, transporting, mixing, and injecting a drug as a solution. The disclosed systems, methods and apparatus may be understood more readily by reference to the following detailed description of particular embodiments and the examples included therein and to the figures and their previous and following description.

It is to be understood that the terminology used herein is for the purpose of describing particular embodiments only, and is not intended to limit the scope of the present disclosure which will be limited only by the appended claims.

It must be noted that as used herein and in the appended claims, the singular forms "a", "an," and "the" include plural reference unless the context clearly dictates otherwise. Thus, for example, reference to "a nucleic acid sequence" includes a plurality of nucleotides that are formed, reference to "the nucleic acid sequence" is a reference to one or more nucleic acid sequences and equivalents thereof known to those skilled in the art, and so forth.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. The term "about" as used herein when referring to a measurable value such as an amount, a temporal duration, and the like, is meant to encompass variations of ±20%, ±10%, ±5%, ±1%, ±0.5%, or ±0.1% from the specified value, as such variations are appropriate to perform the disclosed methods.

"Optional" or "optionally" means that the subsequently described event, circumstance, or material may or may not occur or be present, and that the description includes instances where the event, circumstance, or material occurs or is present and instances where it does not occur or is not present.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in some embodiments, to A without B (optionally including elements other than B); in another embodiments, to B without A (optionally including elements other than A); in yet another embodiments, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of." "Consisting essentially of," when used in the claims, shall have its ordinary meaning as used in the field of patent law.

The term "pharmaceutically acceptable carrier" or "pharmaceutically acceptable diluent" as used herein is meant to refer to an excipient, carrier or diluent that can be administered to a subject, together with an agent or the pharmaceutical compositions disclosed herein, and which is inert or fails to eliminate the pharmacological activity of the active agent of the pharmaceutical composition. In some embodiments, the pharmaceutically acceptable carrier does fails to destroy or is incapable of eliminating the pharmacological activity of an active agent/vaccine and is nontoxic when administered in doses sufficient to deliver a therapeutic amount of the active agent. The term "pharmaceutically acceptable salt" of nucleic acids as used herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenyiacetic, alkanoic such as acetic, HOOC—$(CH_2)$n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled viral specific antigens or polynucleotides provided herein, including those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

As used herein, the terms "prevent" or "preventing," and the like, are meant to refer to reducing the probability of developing a disease or condition in a subject, who does not have, but is at risk of or susceptible to developing a disease or condition.

As used herein, the terms "subject," "individual," "host," and "patient," are used interchangeably herein and refer to a vertebrate individual, including but not limited to a mammal or human, for whom diagnosis, treatment or therapy is desired, particularly humans. Mammals include, but are not limited to, murines, simians, humans, farm animals, cows, pigs, goats, sheep, horses, dogs, sport animals, and pets. The methods described herein are applicable to both human therapy and veterinary applications. In some instances in the description of the present disclosure, the term "patient" refers to human patients suffering from a particular disease or disorder. In some embodiments, the subject is a mammal, and, in other embodiments, the subject is a human.

The terms "treat," "treated," "treating," "treatment," and the like as used herein are meant to refer to reducing or ameliorating a disorder and/or symptoms associated therewith (e.g., a viral infection). "Treating" can refer to administration of the DNA vaccines described herein to a subject after the onset, or suspected onset, of a viral infection. "Treating" includes the concepts of "alleviating," which refers to lessening the frequency of occurrence or recurrence, or the severity, of any symptoms or other ill effects related to a virus and/or the side effects associated with viral therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

For any therapeutic agent described herein the therapeutically effective amount may be initially determined from preliminary in vitro studies and/or animal models. A therapeutically effective dose may also be determined from human data. The applied dose can be adjusted based on the relative bioavailability and potency of the administered agent. Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below. Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained. Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

As used herein, the terms "comprising" (and any form of comprising, such as "comprise," "comprises," and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "about" means that the numerical value is approximate and small variations would not significantly affect the practice of the disclosed embodiments. The term "about" as used herein when referring to a measurable value such as an amount, a temporal duration, and the like, is meant to encompass variations of ±10%, ±5%, ±1%, or ±0.1% from the specified value, as such variations are appropriate to perform the disclosed methods. Where a numerical limitation is used, unless indicated otherwise by the context, "about" means the numerical value can vary by ±10%, ±5%, ±4%, ±3%, ±2%, or ±1% and remain within the scope of the disclosed embodiments.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various embodiments, a preparation can be administered therapeutically; that is, administered to treat an existing disease or condition. In further various embodiments, a preparation can be administered prophylactically; that is, administered for prevention of a disease or condition. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection.

As used herein, the terms "optional" or "optionally" mean that the subsequently described event or circumstance can or cannot occur, and that the description includes instances where said event or circumstance occurs and instances where it does not.

As used herein, the term "diagnosed" means having been subjected to a physical examination by a person of skill, for example, a physician, and found to have a condition that can be diagnosed or treated by the compounds, compositions, or methods disclosed herein.

The disclosure relates to systems, methods and apparatus for storing, transporting, mixing, and injecting a drug as a solution. The disclosed systems, methods and apparatus may be understood more readily by reference to the following detailed description of particular embodiments and the examples included therein and to the figures and their previous and following description.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

The term "compartment" as used herein refers to a space defined by one or more contiguous surfaces that form an internal volume separated from an outside environment by the one or more surfaces. In some embodiments, the compartment is defined by the one or plurality of surface and can be any shaped volume such as a rectangular prism or cylindrical space. The disclosure generally relates to a device comprising a first, second and/or third compartments that comprise cylindrical or substantially cyndrical cavities or a space with walls aligned in sequence such that at least one end of the cylindrical or substantially cylindrical space is adjacent to or proximal to at least one end of the other compartments such cylindrically aligned compartments defining an interior of the device. In some embodiments, the compartments are part of a closed system once aligned and affixed via physical connection between the interior or exterior portion or portions of the surface or surfaces.

The terms "active agent" as used herein refers to a drug or other substance that treats a subject upon administration. In some embodiments, the active agent or derivative thereof is chosen from one or a combination of:

| Active Agent | Dosage* |
|---|---|
| Hydrocortisone sodium succinate | 50 mg/ml to 150 mg/ml |
| Certolizumab pegol | 100 mg/ml to 300 mg/ml |
| Etanercept | 10 mg/ml to 100 mg/ml |
| Risperidone | 2.5 mg/ml to 200 mg/ml |
| Olanzapine pamoate | 1 mg/ml to 200 mg/ml |
| Aripiprazole | 100 mg/ml to 250 mg/ml |
| Human chorionic gonadotropin | 250 IU/ml to 1000 IU/ml |
| Follicle-stimulating hormone | 300 IU/ml to 1000 IU/ml |
| Gonadotropin releasing hormone analogs | 10 mg/ml to 50 mg/ml |
| Azacitidine | 10 mg/ml to 100 mg/ml |
| Metreleptin | 1 mg/ml to 50 mg/ml |
| Various antivenoms including Apis mellifera, Dolichovespula maculata venom protein, Dolichovespula arenaria, Vespula vulgaris, Polistes Fuscatus, Dolichovespula maculata venom protein, Vespula vulgaris venom protein | 0.001 mg/ml to 1 mg/ml |
| Various antibiotics | Various based on patient weight and treatment |
| Romiplostim | 0.1 mg/ml to 1 mg/ml |
| Pralidoxime chloride | 100 mg/ml to 500 mg/ml |
| Ziprasidone mesylate | 5 mg/ml to 10 mg/ml |
| Omacetaxine mepesuccinate | 1 mg/ml to 50 mg/ml |
| Galcanezumab-gnlm | 10 mg/ml to 200 mg/ml |
| Deferoxamine mesylate | 50 mg/ml to 500 mg/ml |
| Methotrexate sodium | 5 mg/ml to 100 mg/ml |
| Cosyntropin | 0.1 mg/ml to 1 mg/ml |
| Peginterferon alfa-2b | 0.1 mg/ml to 1 mg/ml |
| Bortezomib | 0.1 mg/ml to 4 mg/ml |
| Canakinumab | 25 mg/ml to 300 mg/ml |
| Rilonacept | 30 mg/ml to 200 mg/ml |
| Tedglutide | 1 mg/ml to 25 mg/ml |

*Dosages are set forth in the approximate amounts. Any dosage should be interpreted to mean "from about X to about Y." As an example the dosage of hydrocortisone sodium succinate should be from about 50 milligram per milliliter to about 150 milligrams per milliliter.

The terms "movable element" is meant to refer to a shaft. plunger, rod, fastener, or other component or element of the device that is movable in any direction relative to a longitudinal axis of the device. If the device is cylindrical, the longitudinal axis defines a center point in a circumference about the device.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

The terms "disease" as used herein to an ailment of a subject that cause dysfunctional process of the body. In some embodiments, the disease is one or a combination of disease selected from Table 2.

TABLE 2

| Conditions that can lead to cortisol depletion |
|---|
| Addison's Disease |
| Autoimmune adrenalitis |
| Congenital Adrenal Hyperplasia |
| Adrenalectomy |
| Adrenomyeloneuropathy |
| Adrenoleukodystrophy |
| Adrenal Tumors |
| Schmidt Syndrome |
| Hyperaldosteronism |
| Pituitary Tumors |
| Pituitary Cysts |
| Critical-illness Related Corticosteroid Insufficiency |

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used. The comprise the compounds in a pharmaceutically acceptable pharmaceutical compositions carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa, 1995. The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in "Remington's Pharmaceutical Sciences" by E. W. Martin, which is incorporated herein by reference in its entirety.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent. Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agaragar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hardfilled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, catainionic vesicles, and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present disclosure is not entitled to antedate such disclosure by virtue of prior disclosure. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Numerous possible embodiments of the disclosure are envisioned and described in more detail herein. Without deviating from the gravamen of the present disclosure, and staying within the disclosed purposes and functions of this disclosure, minor variations on the physical attributes of the components may be made to engineer a commercial product for various goals, including cost-containment, chemical compatibility, ease-of-use, manufacturing costs and convenience, various medications, and target disease indications. For instance, the disclosed devices can be utilized with various medications, including but not limited to Solu-Cortef®, hydrocortisone, Methylprednisolone for Multiple Sclerosis, chemotherapies for certain cancers, chronic treatment medications for autoimmune conditions, biologic treatments, Glucagon for hypoglycemic emergencies, Ticarcillin for high morbidity infections, Chlordiazepoxide for alcohol withdrawal symptoms, and Desoxycorticosterone pivalate for veterinary emergencies, among others.

Some embodiments of the present disclosure benefit patients living with Congenital Adrenal Hyperplasia (CAH), Addison's disease, and idiopathic adrenal insufficiency in the administration of their medication, such as in times of adrenal crisis. Some embodiments of the disclosure are projected to improve the administration efficacy of lifesaving injectable medication, such as for the 144 million people worldwide living with CAH, Addison's disease, and idiopathic adrenal insufficiency. Some exemplary embodiments of the disclosure require as few as four steps for injection and can be designed for people experiencing an adrenal crisis and their caregivers. For example, exemplary embodiments of the disclosure can improve efficacy specifically of Solu-Cortef® medication with a primary indication of use in patients with CAH.

In some embodiments, the disclosure provides a device comprising: (1) the transportation assembly comprises a main tube and a handle fixed at a mixing end of the main tube opposite of an injection end of the main tube; (2) the storage assembly is adapted to fit within a tube bore of the main tube and comprises a first seal, a liquid-impermeable plug adapted to fit within the first seal, a liquid ejector plunger adapted to couple the first seal and liquid-impermeable plug, a drug container adapted to contain an unmixed medication, a foil seal attached to a liquid-ejection side of the drug container, a second seal adapted to couple to an injection side of drug container opposite of the liquid-ejection side, and optionally an air filter adapted to be placed between the second seal and the injection side of the drug container; (3) the mixture assembly is adapted to attach to the handle and partially fit within the tube bore of the main tube, is adapted to engage the storage assembly, and comprises a twist cap including internal threading and rotatably engaging the handle, a plunger primer engaging the twist cap, and a mixing spring engaging the primer, wherein the primer has flanges located within the internal threading, the primer traverses a cap bore of the twist cap, a handle bore of the handle, and the tube bore of the main tube, and the mixing spring is adapted to fit within the tube bore of the main tube and between the primer and the first seal of the storage assembly; and (4) the injection assembly is adapted to engage the injection end of the main tube and partially fit within the tube bore of the main tube, is adapted to engage the storage assembly, and comprises a protective cap, a cap spring, a hollow needle, a needle driver, and an injection spring, wherein the protective cap is adapted to movably cover an injection tip of the needle, the cap spring is adapted to be positioned between the protective cap and the needle driver and is adapted to be compressed to displace the protective cap to uncover the injection tip of the needle, the needle traverses and is integrated within the needle driver, the needle traverses a tube closure at the injection end of the tube bore of the main tube, and the injection spring is adapted to be positioned between the tube closure and the second seal of the storage assembly, wherein the needle is adapted to puncture the second seal upon fully compressing the protective cap against the needle driver and the needle driver against the injection end of the main tube.

In some embodiments, the device or apparatus of the disclosure is used to conveniently transport and properly store the drug within the device or apparatus until the drug is needed by the patient, at which time the apparatus is used to administer the drug to the patient. To administer the drug to the patient, the drug must be mixed with a liquid, such as water, to prepare a drug-in-solution mixture. To use the mixture assembly to mix the drug, the user twists the twist cap relative to the handle, causing the flanges of the plunger primer to rotate within the threading, causing the primer to move toward and compress the mixing spring, causing the mixing spring to apply pressure to the first seal and propel the liquid ejector plunger toward the drug container. As the liquid ejector plunger moves toward the drug container, the liquid ejector plunger punctures the foil seal and enters into a container bore of the drug container, causing a liquid stored in the main tube between the first seal and foil seal to enter the drug container and mix with the unmixed medication to create a drug-in-solution. Movement of the liquid ejector plunger toward and against the drug container creates liquid pressure that forces the drug-in-solution through the drug container toward the injection end of the main tube and pushes the second seal toward the tube closure, thereby compressing the injection spring. Displacement of the second seal toward the tube closure creates a chamber between the second seal (proximate the injection end) and the drug container (proximate the mixing end), and the chamber contains the drug-in-solution under pressure of the injection spring against the second seal. The injection assembly optionally further comprises a safety device, such as a removable safety clip, that is adapted to be attached to the needle driver, the protective cap, and/or the main tube to prevent the protective cap and the needle driver from moving to compress the cap spring and uncover the injection tip of the needle, and to prevent the needle driver from moving toward the main tube and puncturing the second seal. The safety device may be disengaged, such as by removal of the safety clip, to allow engagement of the injection assembly. Upon removal of the removable safety clip, the apparatus is ready to have the protective cap be pressed against the patient, such as against the patient's bare skin. In the absence of the removable safety clip, pressing the protective cap against the patient causes the protective cap to retract toward the needle drive, causes the needle driver to retract toward the main tube, and causes the needle driver to drive the needle inward into the tube bore of the main tube. If the mixture assembly has been used to mix the drug, then the drug-in-solution is in the chamber awaiting injection into the patient, and driving the needle inward will cause an input tip of the needle to puncture the second seal. The input tip of the needle then enters the chamber, allowing the drug-in-solution to enter a needle bore of the hollow needle and drain the drug-in-solution from the chamber. The drug-in-solution enters the input tip of the needle, traverses the needle bore, and exits the needle at the injection tip. The injection spring, having been compressed by the mixing steps of using the mixture assembly, applies pressure to the second seal to move the second seal back toward the drug container, reducing a chamber volume of the chamber, and pushing the drug-in-solution out of the chamber, through the needle, out of the injection tip, and into the patient.

Further aspects of the disclosure are set forth herein. The details of exemplary embodiments of the disclosure are set forth in the accompanying drawings and the description below. Other features, objects, and advantages of the invention will be apparent from the description and drawings, and from the claims.

In some embodiments, in the disclosed device: (1) the transportation assembly comprises a main tube and a spring plunger screwed into the main tube at a mixing end of the main tube opposite of an injection end of the main tube; (2) the storage assembly is adapted to it within a tube bore of the main tube and comprises a first seal, a liquid-impermeable plug adapted to fit within the first seal, a liquid ejector plunger adapted to couple the first seal and liquid-impermeable plug, a drug container adapted to contain an unmixed medication, a foil seal attached to a liquid-ejection side of the drug container, a second seal adapted to couple to an injection side of drug container opposite of the liquid-ejection side, and optionally an air filter adapted to be placed between the second seal and the injection side of the drug container; (3) the mixture assembly is adapted to attach to the main tube and partially fit within the tube bore of the main tube, is adapted to engage the storage assembly, and comprises a push rod having a recessed annular cavity and slidably engaging the main tube, wherein the push rod traverses a tube opening of the tube bore of the main tube, the push rod is adapted to fit within the tube bore of the main tube and against the plunger and the first seal of the storage assembly, and the spring plunger of the transportation assembly is adapted to engage the recessed annular cavity when the push rod is pushed further into the tube bore of the main tube, from an un-pushed position to a pushed position to mix the drug and liquid; and (4) the injection assembly is adapted to engage the injection end of the main tube and partially fit within the tube bore of the main tube, is adapted to engage the storage assembly, and comprises a hollow needle, a needle driver, a tube plug, and an injection spring, wherein the needle traverses and is integrated within the needle driver, the needle driver is adapted to slide over the injection end of the main tube, the needle traverses the tube plug, which comprises a tube closure at the injection end of the tube bore of the main tube, and the injection spring is adapted to be positioned between the tube closure and the second seal of the storage assembly, wherein the needle is adapted to puncture the second seal upon fully compressing the needle driver against the injection end of the main tube. In some embodiments, the second seal may comprise a chamber piston having an interior cavity with a piston center hole proximate the drug container, a septa placed within the interior cavity and coving the piston center hole, and a spring guide placed within the interior cavity and covering the septa, in which the spring guide includes a guide center hole and engages the injection spring of the injection assembly.

In some embodiments, the disclosed device or apparatus is used to conveniently transport and properly store the drug within the device or apparatus until the drug is needed by the patient, at which time the apparatus is used to administer the drug to the patient. In some embodiments, the needle driver is adapted to be transported and stored detached from the rest of the apparatus until the apparatus is used. The detached needle driver optionally may include tip protectors at the injection tip and the input tip to protect the tips and protect users against accidental needle pricks. When the drug is to be administered to the patient, the drug must be mixed, the needle driver is prepared for use (e.g., removal of any tip protectors and sterile packaging), the needle driver is held by its sidewalls, the injection tip of the needle is inserted into the patient (preferably with the patient's skin flush against a surface of the needle driver proximate the injection tip), and the needle driver is slid onto the injection end of the main tube to cause the input tip of the needle to puncture the second seal and to cause the drug-in-solution to drain from the chamber. In some embodiments, the needle driver is slid onto the main tube, beginning the release the drug-in-solution, before the injection tip of the needle is inserted into the patient's skin.

Prior to administering the drug to the patient, the drug must be mixed with a liquid, such as water, to prepare a drug-in-solution mixture. To use the mixture assembly to mix the drug in the second particular embodiment, the user pushes the push rod relative to the main tube, until the recessed annular cavity reaches the spring plunger, causing the spring plunger to extend into the recessed annular cavity and lock the push rod in place. Pushing the push rod causes the liquid ejector plunger to move toward to apply pressure to the first seal and propel the liquid ejector plunger toward the drug container. As the liquid ejector plunger moves toward the drug container, the liquid ejector plunger punctures the foil seal and enters into a container bore of the drug container, causing a liquid stored in the main tube between the first seal and foil seal to enter the drug container and mix with the unmixed medication to create a drug-in-solution. Movement of the liquid ejector plunger toward and against the drug container creates liquid pressure that forces the drug-in-solution through the drug container toward the injection end of the main tube and pushes the second seal toward the tube closure, thereby compressing the injection spring. Displacement of the second seal toward the tube closure creates a chamber between the second seal (proximate the injection end) and the drug container (proximate the mixing end), and the chamber contains the drug-in-solution under pressure of the injection spring against the second seal. The injection assembly optionally further comprises a safety device, such as a removable safety cap, that is adapted to be attached to the main tube to protect the tube closure at the injection end. The safety device may be disengaged, such as by removal of the safety cap, to allow engagement of the injection assembly. Upon removal of the removable safety device, the apparatus is ready to have the needle driver be pressed against the patient, such as flush against the patient's bare skin, with the needle piercing the patient's skin to the desired depth determined by the length of the needle extending beyond the needle driver, from the injection tip to the surface of the needle driver proximate the injection tip. Pressing the needle driver against the patient may be in conjunction with, and to cause, sliding of the needle driver onto the main tube, thereby causing the needle driver to drive the needle inward into the tube bore of the main tube. Assuming the mixture assembly has been used to mix the drug, the drug-in-solution is in the chamber awaiting injection into the patient, and driving the needle inward will cause an input tip of the needle to puncture the second seal. The input tip of the needle then enters the chamber, allowing the drug-in-solution to enter a needle bore of the hollow needle and drain the drug-in-solution from the chamber. The drug-in-solution enters the input tip of the needle, traverses the needle bore, and exits the needle at the injection tip. The injection spring, having been compressed by the mixing steps of using the mixture assembly, applies pressure to the second seal to move the second seal back toward the drug container, reducing a chamber volume of the chamber, and pushing the drug-in-solution out of the chamber, through the needle, out of the injection tip, and into the patient. Alternatively, the needle driver may be slid onto the main tube, beginning the release the drug-in-solution, before the injection tip of the needle is inserted into the patient's skin.

Further aspects of the disclosure are set forth herein. The details of exemplary embodiments of the disclosure are set forth in the accompanying drawings and the description below. Other features, objects, and advantages of the invention will be apparent from the description and drawings, and from the claims.

Figure 1B:
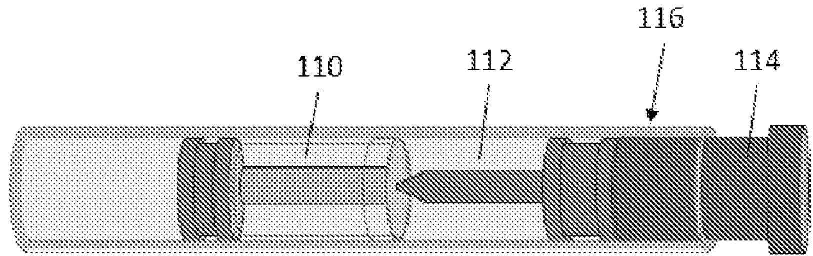
FIG. 1B shows a side cross sectional view of the device of FIG. 1A in which the materials contained in each chamber are combined through the action of a compression mechanism. 116: Three chambered system allowing for the containment and mixing of one or more solid or liquid materials. 112: First chamber that contains a liquid or solid material, which is separated from a second chamber 110 by a barrier. 110: Second chamber that contains a liquid, solid, semisolid or gaseous material. This chamber is separated from chamber 112 by a barrier. 114: A compression system, such as a plunger, spring, screw system, or a combination of two or more of these systems, to activate mixing between chambers 112 and 110.

Referring now to FIG. 1A and FIG. 1B. FIG. 1A shows a side cross sectional view of one embodiment of the device disclosed herein. An assembly 100 contains two chambers, a first chamber 102 and a second chamber 104, that are separated by a seal that, in an unactivated state, prevent material transfer between the two chambers. The first chamber 102 contains a material, either a liquid, solid, semisolid, or gas, to be combined with another material contained in the second chamber 104. The material contained within the second chamber 104 may also be a liquid, solid, semisolid, or gas. Upon activation, the material situated within the first chamber 102 is pushed through the second chamber 104, whereby the material situated within the second chamber 104 is combined with the material from the first chamber 102. These materials are combined through the action of a compression mechanism 114, shown in FIG. 1B. Compression mechanism 114 moves the material from the first chamber 112 (equal to 102 in FIG. 1A) to the second chamber 110 (equal to 104 in FIG. 1A).

Referring now to FIG. 2A. FIG. 2A shows a side cross sectional view of another embodiment of the device disclosed herein. The device in FIG. 2A further comprises moveable components, chamber barriers, seals, and other components associated with an auto-injector. The device assembly 200 is comprised of a housing 218 that contains the three chambers and associated components. The device contains a compression assembly 202 that interacts with an insertion rod 204. This insertion rod pushes through the first chamber 216 to penetrate a chamber seal 206. The chamber seal 206 is an impermeable membrane preventing material transfer between the first chamber 216 and the second chamber 208. Upon device activation and subsequent compression of the compression assembly 202, the insertion rod 204 penetrates the seal 206 and forces material from the first chamber 216 through penetrated seal 206 and into the second chamber 208. As material from the first chamber 216 moves into the second chamber 208, it is combined with the material in the second chamber 208 and moves together into the third chamber 210. As the combined materials move into the third chamber 210, they collectively push seal assembly 214 into the third chamber 210. As seal assembly 214 is pushed inward into the third chamber 210, spring 212 is compressed, which stores energy that will later be used to drive the materials out of the device through the needle for injection.

Referring now to FIG. 2B, which shows a side cross sectional view of another embodiment of the device disclosed herein where the insertion rod that breaks the seal (220, 254) is two components instead of one. Device assembly 220 contains a housing 256, three chambers (the first chamber 254, the second chamber 234, and the third chamber 240), an insertion rod assembly 260 that is comprised of multiple components including an inner insertion rod 224, outer housing 258 and seal 226. Inner insertion rod 224 is further comprised of a fluid path 230 and fluid vent 228 that allow for fluid transfer between the first chamber 254 and the second chamber 234. As compression mechanism 222 pushes inward onto assembly 260, the inner assembly rod pushes into and penetrates seal 232. Upon penetration of seal 232, fluid can either enter fluid vent 228 and pass through fluid path 230 into the second chamber 234, or fluid can move in the reverse direction from the second chamber 234 through fluid path 230 and out fluid vent 228. Once inner insertion rod 224 has penetrated seal 232 and backside becomes flush with outer assembly 258, the entire assembly 260 is compressed by compression mechanism 222 into the second chamber 234. The insertion component on the inner rod will move entirely into the second chamber 234 and the outer assembly and larger component of the insertion rod will rest flush against the outside of the second chamber 234. During this compression material from the first chamber 254 moves through the first chamber 254 and is combined with the material in the second chamber 234. Optional seals 250 around chamber housing 236 prevent material flow outside the chamber. The combined materials are then pushed into the third chamber 240. As the combined materials are pushed into the third chamber 240, moveable seal assembly 246 moves inward into the third chamber 240 creating space for the combined materials. Moveable seal assembly 246 is comprised of seals 238 and housing 262 that is a needle guide and attachment point for spring 244.

As assembly 246 moves into the third chamber 240, seal 248 is pierced by the non-injection side of injection needle 242. This allows fluid to enter injection needle 242 provided the injection end of needle 242 is open. Spring 244 is compressed as assembly 246 moves inward into the third chamber 240. The compressive force of spring 244 will be used to inject the combined materials.

Referring now to FIG. 3A, shows a side cross sectional view of another embodiment of the device disclosed herein with a needle assembly having a needle guard 302 attached to the main device 300. In some embodiments, the needle assembly and guard is attached to the device through a threaded system, but it could also be attached through glue, welding, snap fits, compression fits or other known attachment methods in the art.

A more detailed view of the needle assembly and guard of this embodiment is shown in FIG. 3B. In this condition, the device has not been activated and no component combination has occurred. Needle guard 304 is comprised of a housing 306 that is held in an extended position covering needle 308 by spring 312. The injection end of the needle is covered by seal 314, which prevents fluid from entering or leaving the needle until the guard 304 is retracted and the needle 308 is exposed through seal 314. To activate the needle guard 304, safety pin 310 is removed from the device, which allows housing 306 to be retracted over the device housing thereby exposing the needle 308. Upon retraction of needle guard 316, as shown in FIG. 3C, needle 318 is exposed as needle housing 320 is retracted and needle 318 has penetrated seal 322, allowing material to be injected. In the condition shown in FIG. 3C, the device has been activated and components combined, but injection has not yet begun.

FIG. 3D shows yet another more detailed embodiment of the needle guard 323 and assembly 322. Guard housing 324 is guided through movements by guides 328 that align with and lay in guide tracks 326. Needle 342 is held in place by needle attachment 330. Needle 342 is sealed at the injection end by seal 346, which prevents fluid from entering or leaving the device until needle guard housing 322 is retracted to expose needle 342. To activate the needle guard, safety clip 338 is removed, which allows assembly 322 to retract and expose the needle through seal 346. After injection, spring 344 pushes the needle guide back into place to conceal the needle.

Referring now to FIG. 3E, which shows another embodiment of the needle assembly and needle guard where needle guard 348 consists of housing 350 and is guided through movements by the body of the device 352. The injection end of the needle is sealed through seal 354.

Referring now to FIG. 4, which shows a side cross sectional view of another embodiment with the device body, needle assembly and guard attached. Needle assembly and guard 400 are attached to the main device body 424 through attachment points 404. Attachment may be threads, glue, welds, press fit, snap fit or other commonly known method in the art. The device body consists of an activation mechanism 426 and three chambers (the first chamber 418, the second chamber 436, and the third chamber 444), all contained within housing 420. Insertion rod 428 is contained within the first chamber 418, and optionally contains seal 430. Fluid path 432 and fluid vent 422 are contained within insertion rod 428. The end of insertion rod 428 is adjacent to barrier 434, which separates the first chamber 418 and the second chamber 436. The second chamber 436 is contained within housing 438, which may contain seals 414 or may be a component of the housing itself. The second chamber 436 is maintained separate from the third chamber 444 through moveable seal assembly 410 and optional seal 440. Seal 412 is attached to moveable seal assembly 410 and prevents material from entering needle 448 prior to device activation.

Upon device activation, compression mechanism 426 pushes insertion rod 428 through barrier 434 and into the second chamber 436. Insertion rod 428 enters the second chamber 436 through opening 416, which allows for material transfer and possible seating of insertion rod 428. Material from the second chamber 436 and the first chamber 418 move through the second chamber 436 and moveable seal assembly 410 moves into the third chamber 444 to compress spring 408. The combined material resides inside the third chamber 444 until needle guard assembly 400 is retracted for injection.

To allow for injection after device activation, safety clip 442 is removed, allowing needle guard 400 to retract and expose needle 448. Prior to retraction of needle guard 400, the injection end of the needle is sealed by seal 450, which prevents material from entering or leaving needle 448. Upon retraction, needle 448 is exposed through needle port 452. During retraction, needle guides 446 follow needle guide tracks 402 to allow for proper needle guard movement. Needle 448 is attached through needle attachment 406.

The device of the disclosure can be maintained in 4 different operable conditions, shown in FIG. 5A-5D. Referring to FIG. 5A, the first operable condition 500 is before device activation where no material combination has occurred. Compression mechanism 514 has not been activated and has not compressed insertion rod 512. The first chamber 510 contains the first material to be combined and seal 516 has not been penetrated. The second chamber 508 contains all material to be combined. Moveable seal assembly 506 is acting as a barrier between the second chambers 508 and the third chamber 504, and no material has entered the third chamber 504. Safety pin 518 is still in place on the device and the needle guard has not been retracted.

Referring to FIG. 5B, in the second operable condition, compression assembly 544 has been partially activated. The insertion rod has penetrated into the first chamber 546 by breaking seal 548. The first chambers 546 and the second chamber 550 are in fluid communication but the materials are not fully combined.

Referring to FIG. 5C, in the third operable condition 520, compression assembly 524 has been fully activated and has pushed insertion rod 526 into the first chamber 527. Materials have been combined and moved into the second chamber 522. Moveable seal 528 has retracted and compressed spring 530. Safety pin 529 is in place, needle guard 532 has not been retracted and seal 534 has not been penetrated by the injection needle.

Referring to FIG. 5D, in the fourth operable condition 536, the safety pin has been removed and the needle guard 538 has been retracted, exposing injection needle 544. Spring 542 has pushed back into the device and fluid has been driven out of needle 544. Moveable seal 540 has been pushed back towards the middle of the device.

Referring now to FIG. 6 which shows the three main operable conditions plus the final state when the device is removed from the injection site. Prior to injection 600, the device is brought close to the surface for injection. Once at or near the injection surface 602, the pin is removed and then the device is pushed downward 604 pushing the needle through the injection surface. After injection 606 is complete, the device is lifted and the needle guard conceals the needle again.

Referring now to FIG. 7 which shows one embodiment of internal components of the second chamber 722 and how it resides between the other two chambers (the first chamber 714 and the third chamber 728). The second chamber 722 is contained within housing 706, which is itself contained within housing 700 and optionally surrounded by seals 710. Insertion rod 716 is initially held adjacent seal 712. Insertion rod 716 contains a fluid path 718 and a piercing end for penetrating seal 712. The piercing end 720 may have one or more pointed or blunt protrusions to allow for easier penetration of seal 712. Once seal 712 is penetrated the insertion rod pushes into the second chamber 722 through opening 708 that may be beveled or otherwise shaped for ease of insertion rod entry and material transfer from the first chamber 714 to the second chamber 722. As material from the first chamber 714 is pushed into and through the second chamber 722, moveable seal assembly 724 and needle seal 704 move into the third chamber 728 to allow for material transfer into the third chamber 728. Upon movement into the third chamber 728, spring 702 is compressed and needle seal 704 is pierced by the non-injection side of needle 726, allowing material to enter the needle during injection.

Referring now to FIG. 8, which shows a side cross sectional view of one embodiment of the device disclosed herein which uses a screw mechanism to drive a plunger downward. Assembly 800 shows a device that is not activated and, upon turning in assembly 802, the assembly drives a plunger into the device to compress the components and activate the device.

The devices described herein may be embodied in specific articles of various dimensions, using components of various dimensions, and applied in use according to various operating parameters, for various purposes.

Those dimensional features and parameters of use, which may be the subject of to selection for a particular purpose may include the force applied to the injection site for injecting the active agent, the volume of medicament to be delivered, the size of the internal passage through the needle, the injection depth as determined by the needle length protruding from the device, the spring force applied to the needle to expel the medicament, and the time interval required for injection of the medicament upon actuation of the device. It is believed that these factors individually and/or collectively in various combinations, and possibly others, may contribute to the effectiveness of the device in delivering the medicament into the patient's body, and in dispersion of the medicament from the initial injection site into the surrounding bodily tissues, which may be referred to as the "uptake" of the medicament.

The force applied to the injection site is ultimately determined by how hard the user chooses to press the device against the user's body, but a minimum level of that force is determined by the design of the device and the force required to actuate the device. In some embodiments, the actuation force to release the active agent is between about 4 to about 8 pounds. In some embodiments, the actuation force to release the active agent is between about 2 to about 8 pounds. In some embodiments, the actuation force to release the active agent is between about 4 to about 6 pounds. In some embodiments, the actuation force to release the active agent is between about 2 to about 6 pounds. In some embodiments, the force actually applied by the user is at least about 2 pounds. In some embodiments, the force actually applied by the user is at least about 3 pounds. In some embodiments, the force actually applied by the user is at least about 4 pounds. In some embodiments, the force actually applied by the user is at least about 5 pounds. In some embodiments, the force actually applied by the user is at least about 6 pounds. In some embodiments, the force actually applied by the user is at least about 7 pounds. In some embodiments, the force actually applied by the user is at least about 8 pounds.

The force needed to inject the active agent into a subject may also vary depending on the viscosity of the resultant fluid mixture of the active agent and the pharmaceutically acceptable carrier. In some embodiments, the fluid mixture of the active agent and the pharmaceutically acceptable carrier to be injected by the disclosed device has a viscosity of from about 1 centipoise (cP) to about 150 cP. In some embodiments, the fluid mixture of the active agent and the pharmaceutically acceptable carrier to be injected by the disclosed device has a viscosity of from about 5 cP to about 125 cP. In some embodiments, the fluid mixture of the active agent and the pharmaceutically acceptable carrier to be injected by the disclosed device has a viscosity of from about 10 cP to about 100 cP. In some embodiments, the fluid mixture of the active agent and the pharmaceutically acceptable carrier to be injected by the disclosed device has a viscosity of from about 15 cP to about 75 cP. In some embodiments, the fluid mixture of the active agent and the pharmaceutically acceptable carrier to be injected by the disclosed device has a viscosity of from about 20 cP to about 60 cP. In some embodiments, the fluid mixture of the active agent and the pharmaceutically acceptable carrier to be injected by the disclosed device has a viscosity of from about 25 cP to about 50 cP. In some embodiments, the fluid mixture of the active agent and the pharmaceutically acceptable carrier to be injected by the disclosed device has a viscosity of about 1 cP. In some embodiments, the fluid mixture of the active agent and the pharmaceutically acceptable carrier to be injected by the disclosed device has a viscosity of about 5 cP. In some embodiments, the fluid mixture of the active agent and the pharmaceutically acceptable carrier to be injected by the disclosed device has a viscosity of about 10 cP. In some embodiments, the fluid mixture of the active agent and the pharmaceutically acceptable carrier to be injected by the disclosed device has a viscosity of about 25 cP. In some embodiments, the fluid mixture of the active agent and the pharmaceutically acceptable carrier to be injected by the disclosed device has a viscosity of about 50 cP. In some embodiments, the fluid mixture of the active agent and the pharmaceutically acceptable carrier to be injected by the disclosed device has a viscosity of about 75 cP. In some embodiments, the fluid mixture of the active agent and the pharmaceutically acceptable carrier to be injected by the disclosed device has a viscosity of about 100 cP. In some embodiments, the fluid mixture of the active agent and the pharmaceutically acceptable carrier to be injected by the disclosed device has a viscosity of about 110 cP. In some embodiments, the fluid mixture of the active agent and the pharmaceutically acceptable carrier to be injected by the disclosed device has a viscosity of about 120 cP. In some embodiments, the fluid mixture of the active agent and the pharmaceutically acceptable carrier to be injected by the disclosed device has a viscosity of about 130 cP. In some embodiments, the fluid mixture of the active agent and the pharmaceutically acceptable carrier to be injected by the disclosed device has a viscosity of about 140 cP. In some embodiments, the fluid mixture of the active agent and the pharmaceutically acceptable carrier to be injected by the disclosed device has a viscosity of about 150 cP. In some embodiments, the fluid mixture of the active agent and the pharmaceutically acceptable carrier to be injected by the disclosed device has a viscosity of great than about 150 cP.

The time interval over which the needle is held in place against the injection site after injection is typically based upon manufacturer's recommendations as printed upon the auto-injector label. In some embodiments, a time interval of at least about 2 seconds is recommended. In some embodiments, a time interval of at least about 3 seconds is recommended. In some embodiments, a time interval of at least about 4 seconds is recommended. In some embodiments, a time interval of at least about 5 seconds is recommended.

The volume of medicament to be delivered is dependent upon the internal dimensions of the device which are selected by the manufacturer to administer the desired volume of active agents. For example, when administering epinephrine with an auto-injector, an injected volume of about 0.15 mL or about 0.30 mL may be used. Higher volumes of injectant may also be administered. In some embodiments, from about 0.50 mL to about 3.0 mL volumes may be rapidly injected with any of the disclosed devices, depending upon viscosity and other factors. In these embodiments, references to an injected or dispensed volume of active agent, are referring to the total volume of liquid injected into the patient, and those references are not related to the amount of active ingredient contained in that injected volume. However, in some embodiments, the device of the disclosure may be used to deliver a predetermined amount or dosage of an active agent into a subject. In some embodiments, when cortisone or cortisone derivatives is used, the cortisone or cortisone derivative is used with the disclosed device in a dosage of from about 5 mg to about 500 mg in weight. In some embodiments, the cortisone or cortisone derivative is used with the disclosed device in a dosage of from about 10 mg to about 400 mg in weight. In some embodiments, the cortisone or cortisone derivative is used with the disclosed device in a dosage of from about 25 mg to about 300 mg in weight. In some embodiments, the cortisone or cortisone derivative is used with the disclosed device in a dosage of from about 50 mg to about 250 mg in weight. In some embodiments, the cortisone or cortisone derivative is used with the disclosed device in a dosage of from about 60 mg to about 200 mg in weight. In some embodiments, the cortisone or cortisone derivative is used with the disclosed device in a dosage of from about 75 mg to about 1500 mg in weight. In some embodiments, the cortisone or cortisone derivative is used with the disclosed device in a dosage of from about 5 mg/mL to about 300 mg/mL in a weight to volume solution of active agent in pharmaceutically acceptable carrier. In some embodiments, the cortisone or cortisone derivative is used with the disclosed device in a dosage of from about 10 mg/mL to about 250 mg/mL in a weight to volume solution of active agent in pharmaceutically acceptable carrier. In some embodiments, the cortisone or cortisone derivative is used with the disclosed device in a dosage of from about 15 mg/mL to about 200 mg/mL in a weight to volume solution of active agent in pharmaceutically acceptable carrier. In some embodiments, the cortisone or cortisone derivative is used with the disclosed device in a dosage of from about 20 mg/mL to about 175 mg/mL in a weight to volume solution of active agent in pharmaceutically acceptable carrier. In some embodiments, the cortisone or cortisone derivative is used with the disclosed device in a dosage of from about 25 mg/mL to about 150 mg/mL in a weight to volume solution of active agent in pharmaceutically acceptable carrier. In some embodiments, the cortisone or cortisone derivative is used with the disclosed device in a dosage of from about 30 mg/mL to about 1250 mg/mL in a weight to volume solution of active agent in pharmaceutically acceptable carrier.

It will be appreciated that the amount of active agent, such as cortisone or cortisone derivatives, in an injected volume of medicament may vary. The amount of active agent in that injected volume may differ depending upon the dosage prescribed for the patient. Prescribed dosages of cortisone or cortisone derivative may for example be about 1 mg, about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, or about 300 mg. Those dosages of active agent may be formulated with other ingredients, such as a pharmaceutically acceptable carrier, to comprise a volume of medicament of from 0.15 mL up to about 0.6 mL. The amount of active agent is not necessarily directly related to the volume of medicament to be injected, because the volume can be diluted as desired. For example, 0.30 mL of injected medicament may contain about 1 mg or about 25 mg of active agent.

The size of the internal passage through the needle is determined by the manufacturer by selection of the appropriate gauge of tubing for the needle. Small diameter stainless steel tubing typically used for hypodermic needles can be obtained in various standard sizes referred to as gauges. The gauge determines the nominal outside diameter of the tubing. Then for each gauge the tubing is typically available in various wall thickness referred to as Regular Wall (RW), Thin Wall (TW), Extra Thin Wall (ETW) and Ultra Thin Wall (UTW). The thinner the wall for a given gauge of tubing, the larger the internal diameter or bore of the tubing will be. And for each standard tubing size, such as for example a 22 gauge RW tubing, the applicable standards specify minimum, nominal and maximum values for each dimension such as the internal diameter. For the device of the present disclosure, the needle may be constructed from RW stainless steel tubing of gauges as large as 18 gauge and as small as 24 gauge. Wall thicknesses other than RW could also be selected. The table below shows standard minimum, nominal and maximum inner diameters for 18 to 24 gauge RW stainless steel tubing. All dimensions are given in inches.

| GAUGE | TYPE | MIN I.D. | NOMINAL I.D. | MAX I.D. |
|---|---|---|---|---|
| 18 | RW | 0.0315 | 0.0330 | 0.0345 |
| 19 | RW | 0.0255 | 0.0270 | 0.0285 |
| 20 | RW | 0.0230 | 0.0238 | 0.0245 |
| 21 | RW | 0.0195 | 0.0203 | 0.0210 |
| 22 | RW | 0.0155 | 0.0163 | 0.0170 |
| 23 | RW | 0.0125 | 0.0133 | 0.0140 |
| 24 | RW | 0.0115 | 0.0123 | 0.0130 |

Thus, selecting the smallest of these inner diameters, the minimum inner diameter for the 24 gauge RW tubing is about 0.0115 inch. If the 23 gauge RW tubing is selected, its inner diameter would be at least about 0.0125 inch. If the 22 gauge RW tubing is selected, its inner diameter would be at least about 0.0155 inch. For all of the selections shown in the above table, the inner diameter of the needle would be no greater than about 0.0345 inch, which is the maximum inner diameter for an 18 gauge RW tubing.

The injection depth as determined by the needle length protruding from the disclosed device is illustrated for example in FIG. 6. That dimension is determined by the dimensions of the various internal components as is suitable for the particular active agent to be injected. For example, for subcutaneous injection of an active agent, the device may provide injections in the subcutaneous region wherein the injection is at a depth of from about 0.15 inches to about 0.30 inches in some embodiments. In other embodiments, the injection is at a depth of from about 0.2 inches to about 0.25 inches within the subject. For intramuscular injections of an active agent, the disclosed device may provide injections in the intramuscular region wherein the injection is at a depth of from about 0.4 inches to about 0.7 inches in some embodiments. In other embodiments, the injection is at a depth of about 0.6 inches within the subject. In some embodiments, the disclosed device may provide intramuscular injections at a depth up to about 1.25 inches within the subject.

The spring force applied to expel the active agent is determined by the manufacturer's selection of the power spring, and by the design of the various internal components which will affect how much of the available spring force is actually applied. A given spring, when compressed, will have a certain static force which it applies to the surrounding structure which holds the spring in the compressed state. When the spring is released, however, some of its potential energy will be lost to friction and to moving the needle and collapsing the needle sheath, so that the force the spring actually applies to the plunger to expel the active agent, which can be referred to as a dynamic force applied to the plunger, will be less than the initial static force output of the spring. For example a spring may have a nominal static force output of about 100 Newtons when compressed. Due to manufacturing tolerances the actual static force output of that spring may be in the range of from about 0 to about 100 Newtons. Then the dynamic force that spring actually applies to the plunger to expel the active agent may be in the range of from about 10 to about 75 Newtons. That dynamic force may be described as being at least about 10 Newtons, about 20 Newtons, about 30 Newtons, about 40 Newtons, about 50 Newtons, about 60 Newtons, about 70 Newtons, about 80 Newtons, about 90 Newtons, or about 100 Newtons.

The devices according to the disclosure can be used to deliver a wide range of active agents into a subject. Of particular interest are the active agents provided in Table 1 with the dosage listed therein.

TABLE 1

Active agents suitable for use in the devices of the disclosure and the corresponding dosages.

| Active Agent | Dosage |
|---|---|
| Hydrocortisone sodium succinate | 50 mg/ml to 150 mg/ml |
| Certolizumab pegol | 100 mg/ml to 300 mg/ml |
| Etanercept | 10 mg/ml to 100 mg/ml |
| Risperidone | 2.5 mg/ml to 200 mg/ml |
| Olanzapine pamoate | 1 mg/ml to 200 mg/ml |
| Aripiprazole | 100 mg/ml to 250 mg/ml |
| Human chorionic gonadotropin | 250 IU/ml to 1000 IU/ml |
| Follicle-stimulating hormone | 300 IU/ml to 1000 IU/ml |
| Gonadotropin releasing hormone analogs | 10 mg/ml to 50 mg/ml |
| Azacitidine | 10 mg/ml to 100 mg/ml |
| Metreleptin | 1 mg/ml to 50 mg/ml |
| Various antivenoms including Apis mellifera, Dolichovespula maculata venom protein, Dolichovespula arenaria, Vespula vulgaris, Polistes Fuscatus, Dolichovespula maculata venom protein, Vespula vulgaris venom protein | 0.001 mg/ml to 1 mg/ml |
| Various antibiotics | Various based on patient weight and treatment |
| Romiplostim | 0.1 mg/ml to 1 mg/ml |
| Pralidoxime chloride | 100 mg/ml to 500 mg/ml |
| Ziprasidone mesylate | 5 mg/ml to 10 mg/ml |
| Omacetaxine mepesuccinate | 1 mg/ml to 50 mg/ml |
| Galcanezumab-gnlm | 10 mg/ml to 200 mg/ml |
| Deferoxamine mesylate | 50 mg/ml to 500 mg/ml |
| Methotrexate sodium | 5 mg/ml to 100 mg/ml |
| Cosyntropin | 0.1 mg/ml to 1 mg/ml |
| Peginterferon alfa-2b | 0.1 mg/ml to 1 mg/ml |
| Bortezomib | 0.1 mg/ml to 4 mg/ml |
| Canakinumab | 25 mg/ml to 300 mg/ml |
| Rilonacept | 30 mg/ml to 200 mg/ml |
| Tedglutide | 1 mg/ml to 25 mg/ml |

In some embodiments, the disclosed device is used for delivery of one or a plurality of active agents chosen from Table 1 into a subject. In some embodiments, the disclosed device is used for delivery of one or a plurality of active agents chosen from Table 1 in a dosage identified in Table 1 into a subject. In some embodiments, the disclosed device is used for delivery cortisone into a subject. In some embodiments, the disclosed device is used for delivery a cortisone derivative into a subject. In some embodiments, the disclosed device is used for delivery a hydrocortisone sodium succinate into a subject. In some embodiments, the one or plurality of active agents are delivered into a subject with the disclosed device in the to presence of one or a plurality of pharmaceutically acceptable carriers. In some embodiments, the pharmaceutically acceptable carrier used is water for injection. In some embodiments, the pharmaceutically acceptable carrier used is sterile water for injection. In some embodiments, the pharmaceutically acceptable carrier used is bacteriostatic water for injection. In some embodiments, the pharmaceutically acceptable carrier used is sodium chloride in water. In some embodiments, the pharmaceutically acceptable carrier used is sodium bicarbonate in water. In some embodiments, the pharmaceutically acceptable carrier used is dimethyl sulfoxide solutions in water.

Methods

The disclosure provides methods for treating and/or prevent a disease or disorder in a subject comprising administering one or a plurality of active agents by any of the devices disclosed herein. The disclosure further provides a method of treating a subject in need of administration of one or a plurality of active agents comprising administering a pharmaceutically effective amount of the one or plurality of active agents by any of the disclosed devices. In some embodiments, the subject is diagnosed with, or suspected of having, a cortisol disorder. A "cortisol disorder" as used herein refers to any disease or disorder that causes dysfunction of secretion of cortisol to abnormal levels. In some embodiments, the cortisol disorder is Addison's disease, Congenital adrenal hyperplasia, Autoimmune adrenalitis, Adrenalectomy, Adrenomyeloneuropathy, Adrenoleukodystrophy, Adrenal Tumors, Schmidt Syndrome, Hyperaldosteronism, Pituitary Tumors, Pituitary Cysts, or Critical-illness Related Corticosteroid Insufficiency. In some embodiments, the subject is diagnosed with, suspected of having, or is suffering cortisol depletion. In some embodiments, the cortisol depletion in the subject is caused by Addison's disease, Congenital adrenal hyperplasia, Autoimmune adrenalitis, Adrenalectomy, Adrenomyeloneuropathy, Adrenoleukodystrophy, Adrenal Tumors, Schmidt Syndrome, Hyperaldosteronism, Pituitary Tumors, Pituitary Cysts, or Critical-illness Related Corticosteroid Insufficiency.

Other than cortisone or cortisone derivatives, the disclosed devices can also be used to deliver other non-emergency active agents into a subject in need thereof for needed treatment. Examples of such non-emergency active agents include, but not limited to, non-emergency steroids, antibiotics, analgesics, disease specific treatments (e.g., MS treatments, treatments), insulins, glycoproteins, immunomodulators, G-CSFs, erythropoietin psoriasis (Epogen®, Procrit®), biologics, antihypertensives, vaccines, hormones (including control), anti-hormones, sedatives, antiepileptics, anti-neoplastics, insecticidal agents (e.g., dobutrex), anti-psychotics, detoxing agents, cosmetics, selective serotonin reuptake inhibitors (SSRIs), proton-pump inhibitors (PPIs), anesthetics, diuretics, anti-diuretics, blood thinners (e.g., low molecular heparin), streptokinase, and the like, alone or in combination, whether in a liquid form, reconstitutable form or otherwise. In some embodiments, the devices of the disclosure are used to deliver medications historically using the Act-o-Vial® system, namely Methylprednisolone for Multiple Sclerosis, certain cancers, and autoimmune conditions. In some embodiments, the devices of the disclosure are used to deliver Glucagon used in hypoglycemic emergencies. In some embodiments, the devices of the disclosure are used to deliver Ticarcillin used to treat high morbidity infections. In some embodiments, the devices of the disclosure are used to deliver Chlordiazepoxide used to treat alcohol withdrawal symptoms. In some embodiments, the devices of the disclosure are used to deliver Desoxycorticosterone pivalate used in veterinary emergencies. In some embodiments, the devices of the disclosure are used for in-vitro fertilization treatments.

The devices of the disclosure may be manufactured by any means known to one to skilled in the relevant art, particularly in the field of auto-injectors. In some embodiments, the first, second, and third compartments are physically attached to the housing by friction fit, rivet, plug, or plastic welding such as radio frequency or ultrasonic welding. The compartments may also be attached to the housing or each other via the same techniques or through protrusions such as snap fittings. The components of the device can be plastic, rubber, glass, or metal. Most, if not all, sealing materials will be comprised of a plastic or rubber, whereas the chambers will be comprised of plastic, glass, or metal. The insertion rod will either be plastic or metal and attached to any seals through an interlocking mechanism based on groves for attachment, or attached through a screw-like threading. In embodiments with a moveable system attached to the insertion rod, the moveable system will be attached through frictional forces. Seals attached to the chamber will be press fit in place using frictional forces, attached through an interlocking grove system, or threaded into place. In some embodiments, the compartments are cylindrical or substantially cylindrical with protrusions on ends for fastening. In some embodiments, there may be 1 or more fasteners on each side of a compartment and each side of a device component.

Methods in accordance with aspects of the disclosure include, for instance, a method for using an apparatus for transportation, storage, mixture, and injection of a drug to a patient, wherein the apparatus comprises: a transportation assembly, a storage assembly, a mixture assembly, and an injection assembly, and wherein the method comprises providing the apparatus, engaging the mixture assembly to mix the drug and create a drug-in-solution in preparation to administer the drug to the patient, and engaging the injection assembly to inject the drug-in-solution into the patient. The method may further comprise disengaging a safety device prior to engaging the injection assembly to inject the drug-in-solution into the patient.

Further methods in accordance with aspects of the disclosure include, for instance, a method for assembling an apparatus for transportation, storage, mixture, and injection of a drug to a patient, wherein the apparatus comprises: a transportation assembly, a storage assembly, a mixture assembly, and an injection assembly, and wherein the method comprises: providing and assembling the transportation assembly; providing and assembling the storage assembly, providing and assembling the mixture assembly, and providing and assembling the injection assembly.

Systems in accordance with aspects of the disclosure include, for instance, a system for assembling an apparatus for transportation, storage, mixture, and injection of a drug to a patient, wherein the apparatus comprises: a transportation assembly, a storage assembly, a mixture assembly, and an injection assembly, and wherein the system comprises: means for assembling the transportation assembly; means for assembling the storage assembly, means for assembling the mixture assembly, and means for assembling the injection assembly.

Methods in accordance with aspects of the invention include, for instance, a method for using an apparatus for transportation, storage, mixture, and injection of a drug to a patient, wherein the apparatus comprises: a transportation assembly, a storage assembly, a mixture assembly, and an injection assembly, and wherein the method comprises providing the apparatus, engaging the mixture assembly to mix the drug and create a drug-in-solution in preparation to administer the drug to the patient, and engaging the injection assembly to inject the drug-in-solution into the patient. The method may further comprise disengaging a safety device prior to engaging the injection assembly to inject the drug-in-solution into the patient.

Further methods in accordance with aspects of the invention include, for instance, a method for assembling an apparatus for transportation, storage, mixture, and injection of a drug to a patient, wherein the apparatus comprises: a transportation assembly, a storage assembly, a mixture assembly, and an injection assembly, and wherein the method comprises: providing and assembling the transportation assembly; providing and assembling the storage assembly, providing and assembling the mixture assembly, and providing and assembling the injection assembly.

Systems in accordance with aspects of the invention include, for instance, a system for assembling an apparatus for transportation, storage, mixture, and injection of a drug to a patient, wherein the apparatus comprises: a transportation assembly, a storage assembly, a mixture assembly, and an injection assembly, and wherein the system comprises: means for assembling the transportation assembly; means for assembling the storage assembly, means for assembling the mixture assembly, and means for assembling the injection assembly.

Methods of Making

The device described herein consists of an active agent to be injected into the body and thus must be manufactured using sterile and aseptic techniques. General techniques for manufacturing include sterilization of device components, filling of active and carrier agents, assembly of active agent contacting components, and assembly of non-active agent contacting components. Filling of active agents and carrier agents, as well as assembly of some active agent contacting components, must be completed within an aseptic processing manufacturing facility, often referred to as an aseptic core.

Component sterilization techniques are well known in the art. Filling of agents depends on device characteristics and whether the active agent is a solid or liquid. Liquids can be filled through dispensing techniques using volumetric or flow measurements. Powders and other solids can be filled through insertion of the powder or solid material using density or weight based measurement systems for determining total fill amounts.

In one manufacturing method of this device, a chamber is capped at the distal end using a movable seal, and this capped chamber is then inserted into an aseptic core. Active agent is inserted into this chamber through either a powder filling method or liquid filling method. Liquids may or may not be lyophilized, depending on active agent type and device requirements. This filled chamber is then capped on the proximal end and inserted into the main device tube. The second agent is then filled onto the first chamber using either powder of liquid fill methods, an insertion rod is added, and the exposed end of the second filled chamber is sealed. The needle is added to the device, and the full subassembly is removed from the aseptic core. The remaining components are assembled onto the device outside the aseptic core.

In another manufacturing method, components are sterilized outside of the aseptic core. The needle assembly, movable seals and one chamber are inserted into the main device housing outside the aseptic core. This subassembly is then transferred into an aseptic core where active agent is inserted into the exposed chamber using liquid or powder filling methods. This chamber is capped, and the second active agent is added on top of the first, also using a liquid or powder filling method. An insertion rod and seal are added above the newly filled chamber and the assembly is removed from the aseptic core. Any final manufacturing assembly steps are completed and the device is packaged and labeled for distribution.

In another manufacturing method, the components are sterilized. The main device tube and needle are assembled and inserted into an aseptic core. A device chamber is sealed at the distal end with a moveable seal and placed into the same aseptic core. Active agent is inserted into the chamber using powder filling methods or liquid filling methods. If needed, the liquid is lyophilized. Once filling is complete, the chamber is sealed at the proximal end. The filled and sealed chamber is inserted into the main device tube. Liquid or powder is subsequently filled on top of the previous chamber. An insertion rod and seal are added above the newly filled chamber and the assembly is removed from the aseptic core. Any final manufacturing assembly steps are completed and the device is packaged and labeled for distribution.

In some embodiments, the first, second, and third compartments are physically attached to the housing by friction fit, rivet, plug, or plastic welding such as radio frequency or ultrasonic welding. The compartments may also be attached to the housing or each other via the same techniques or through protrusions such as snap fittings. The components of the device will be plastic, rubber, glass, or metal. In some embodiments, sealing materials will be comprised of a plastic or rubber, whereas the chambers will be comprised of plastic, glass, or metal. In some embodiments, the insertion rod will either be plastic or metal and attached to any seals through an interlocking mechanism based on groves for attachment, or attached through a screw-like threading. In some embodiments with a moveable system attached to the insertion rod, the moveable system will be operably attached through frictional forces. Seals attached to the chamber will be press fit in place using frictional forces, attached through an interlocking grove system, or threaded into place. In some embodiments the compartments are cylindrical or substantially cylindrical with protrusions on ends for fastening. In some embodiments there may be 1 or more fasteners on each side of a compartment and each side of a device component.

The foregoing description discloses exemplary embodiments of the invention. While the invention herein disclosed has been described by means of specific embodiments and applications thereof, numerous modifications and variations could be made thereto by those skilled in the art without departing from the scope of the invention set forth in the claims. Modifications of the above disclosed apparatus and methods that fall within the scope of the claimed invention will be readily apparent to those of ordinary skill in the art. Accordingly, other embodiments may fall within the spirit and scope of the claimed invention, as defined by the claims that follow hereafter.

The disclosure relates to a method of treating a subject in need thereof by administering one or a plurality of active agents in through use of the device. In some embodiments, the method of administering comprises depressing the movable element to a first predetermined position such that the insertion rod punctures the seal on the first opening separating the first and second compartments. In some embodiments, the method further comprises allowing a time to lapse to allow the active agent and diluent in the first and second compartments to mix and dissolve and/or activate the active agent. In some embodiments, the method further comprises a step of depressing the movable element a second sequential time after the first step of depressing to a second predetermined position, such that the insertion rod displaces or punctures the seal separating the second and third compartments. In some embodiments, the method further comprises a step of allowing a second period of time to elapse such that the active agent and pharmaceutically acceptable carrier or diluent contact the end of the needle. In some embodiments, the methods further comprise a step of depressing the movable element a third time to a fully depressed position, such that the spring of the needle assembly releases and deploys the distally facing end of the needle into the subject. In some embodiments, the methods further comprise unlocking the needle assembly before fully depressing the movable element. In some embodiments, the first predetermined distance is from about 1 cm to about 5 centimeters in movement toward the needle assembly. In some embodiment, the second predetermined distance is from about 1 cm to about 5 cm in movement toward the needle assembly. In some embodiments, the third predetermined distance is from about 2 centimeters to 6 centimeters.

In some embodiments, the methods of administration are free of a third depression of the movable element and final release of the spring of the need assembly is accomplished by simply applying pressure to the end of the device proximal to the needle assembly. In such cases, applying pressure to the device in the direction of the longitudinal axis by the subject or operator releases the spring and unsheathes the needle with a force that deploys the pharmaceutical composition into the subject.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

In the description above, numerous specific details are set forth in order to provide a more thorough understanding of embodiments of the invention. It will be apparent, however, to an artisan of ordinary skill that the invention may be practiced without incorporating all aspects of the specific details described herein. Not all possible embodiments of the invention are set forth verbatim herein. A multitude of combinations of aspects of the invention may be formed to create varying embodiments that fall within the scope of the claims hereafter. In addition, specific details well known to those of ordinary skill in the art have not been described in detail so as not to obscure the invention. Readers should note that although examples of the invention are set forth herein, the claims, and the full scope of any equivalents, are what define the metes and bounds of the invention protection.

The foregoing description discloses exemplary embodiments of the disclosure. While the disclosure herein disclosed has been described by means of specific embodiments and applications thereof, numerous modifications and variations could be made thereto by those skilled in the art without departing from the scope of the disclosure set forth in the claims. Modifications of the above disclosed apparatus and methods that fall within the scope of the claimed subject matter will be readily apparent to those of ordinary skill in the art. Accordingly, other embodiments may fall within the spirit and scope of the claimed subject matter, as defined by the claims that follow hereafter.

In the description above, numerous specific details are set forth in order to provide a more thorough understanding of embodiments of the disclosure. It will be apparent, however, to an artisan of ordinary skill that the disclosure may be practiced without incorporating all aspects of the specific details described herein. Not all possible embodiments of the disclosure are set forth verbatim herein. A multitude of combinations of aspects of the disclosure may be formed to create varying embodiments that fall within the scope of the claims hereafter. In addition, specific details well known to those of ordinary skill in the art have not been described in detail so as not to obscure the disclosure. Readers should note that although examples of the disclosure are set forth herein, the claims, and the full scope of any equivalents, are what define the metes and bounds of the protection.

The invention claimed is:

1. A device comprising:

(a) a first compartment and a second compartment, each of the first compartment and the second compartment defining a first cavity and a second cavity, respectively, separated by and in fluid communication with a first opening covered by a first movable seal;

(b) a needle assembly;

(c) an insertion rod positioned in the first compartment operably connected to a movable element; and (d) a third compartment comprising the needle assembly and defining a third cavity adjacent to and separated from the second compartment by a second opening covered by a second movable seal of a movable plug, whereupon depression of the movable element allows for displacement of the insertion rod and the movable plug, wherein displacement of the movable plug provides fluid communication between the second compartment and the third compartment, wherein the needle assembly comprises (i) a spring compressible upon filling of the third compartment and (ii) a needle comprising a first fluid opening within the third cavity and an oppositely facing second fluid opening positioned away from the first cavity and the second cavity.

2. The device of claim 1, wherein the insertion rod comprises two oppositely directed faces, a first face physically in contact with the movable element and a second face positioned within the first cavity, wherein the second face comprises a protrusion.

3. The device of claim 2, wherein the protrusion has a beveled surface.

4. The device of claim 1, wherein the movable element is physically positioned adjacent to the insertion rod, and wherein the insertion rod is movable upon depression of the movable element toward a direction along a longitudinal axis parallel to and within the first compartment and the second compartment.

5. The device of claim 1, wherein the second compartment comprises an active agent and the first compartment comprises a pharmaceutically acceptable carrier; or wherein the second compartment comprises a pharmaceutically acceptable carrier and the first compartment comprises an active agent; or wherein both the first compartment and the second compartment each comprises one or a plurality of active agents.

6. The device of claim 5, wherein both the first compartment and the second compartment each comprises: one or a plurality of active agents and one or a plurality of pharmaceutically acceptable carriers.

7. The device of claim 5, wherein the active agent is lyophilized.

8. The device of claim 1, wherein the second compartment comprises an active agent in solid or semisolid form; and wherein the first compartment comprises a pharmaceutically acceptable carrier in liquid form.

9. The device of claim 1, wherein the second compartment comprises an active agent in liquid form; and wherein the first compartment comprises a pharmaceutically acceptable carrier in liquid form.

10. The device of claim 1, wherein the insertion rod comprises a fluid path extending between two oppositely directed faces, a first face physically in contact with the movable element and a second face positioned within the first cavity, wherein the second face comprises a pointed protrusion and at least one valve distally positioned from the pointed protrusion.

11. The device of claim 1, wherein, in a first operable condition, the movable element is in a fully extended position relative to a lateral orientation of the device, wherein the first compartment comprises a pharmaceutically acceptable carrier, the second compartment comprises one or a plurality of active agents, and wherein the first movable seal and the second movable seal covering each of the first opening and the second opening are fully intact preventing fluid flow from one compartment to another compartment.

12. The device of claim 11, wherein, in a second operable condition, the movable element is in a partially depressed position relative to the lateral orientation of the device, wherein the first compartment and the second compartment comprises a pharmaceutically acceptable carrier and one or a plurality of active agents, and wherein the second movable seal covers the second opening, preventing fluid flow from the third compartment into the first compartment or the second compartment.

13. The device of claim 12, wherein, in a third operable condition, the movable element is in a partially depressed position relative to the lateral orientation of the device such that the insertion rod has punctured the second movable seal, wherein the first compartment, the second compartment, and the third compartment comprise a pharmaceutically acceptable carrier and one or a plurality of active agents, and wherein the second movable seal has been punctured or disposed from a position over the second opening and the needle assembly is exposed to the one or the plurality of active agents and the pharmaceutically acceptable carrier.

14. The device of claim 13, wherein, in a fourth operable condition, the movable element is in a fully depressed position relative to the lateral orientation of the device and the needle of the needle assembly is exposed.

15. A device comprising:

(a) a first compartment, a second compartment, and a third compartment, each of the first compartment, the second compartment, and the third compartment defines a first cavity, a second cavity, and a third cavity, respectively, and the second compartment is adjacently positioned between the first compartment and the third compartment;

(b) a needle guard assembly operably functional within and at least partially housed in the third cavity and comprising a needle operably attached to a spring compressible upon filling of the third compartment; and (c) an insertion rod positioned in the first compartment operably connected to a movable element, the insertion rod and the movable element movable along a longitudinal axis of the first compartment, the second compartment, and the third compartment;

wherein the first compartment and the second compartment are in fluid communication through a first opening, wherein the second compartment and the third compartment are in fluid communication through a second opening; the first opening covered by a first seal and the second opening covered by a second seal; and (i) wherein the first compartment comprises one or a plurality of active agents; and the second compartment comprises one or a plurality of pharmaceutically acceptable carriers; or (ii) wherein the first compartment comprises one or a plurality of pharmaceutically acceptable carriers; and the second compartment comprises one or a plurality of active agents.

16. The device of claim 15, wherein the first compartment, the second compartment, and the third compartment are cylindrically aligned along the longitudinal axis of the first cavity, the second cavity, and the third cavity.

17. The device of claim 15, wherein the needle guard assembly comprises a needle sheath, and an interior surface comprising one or more track elements in operable connection to the needle, wherein the one or more track elements are figured to guide movement of the needle through the needle sheath after movement of the spring.

* * * * *